(12) United States Patent
DiCesare et al.

(10) Patent No.: US 9,581,491 B2
(45) Date of Patent: Feb. 28, 2017

(54) FLOW CELL MODULES AND LIQUID SAMPLE ANALYZERS AND METHODS INCLUDING SAME

(71) Applicant: PerkinElmer Health Sciences, Inc., Waltham, MA (US)

(72) Inventors: Joseph L. DiCesare, Redding, CT (US); Feng Jin, Milford, CT (US); Timothy P. Neal, Harwinton, CT (US); David Aikens, Chester, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 80 days.

(21) Appl. No.: 14/501,544

(22) Filed: Sep. 30, 2014

(65) Prior Publication Data

US 2016/0091365 A1 Mar. 31, 2016

(51) Int. Cl.
*G01J 3/02* (2006.01)
*G01J 3/44* (2006.01)
*G02B 6/26* (2006.01)
*G01N 21/05* (2006.01)
(Continued)

(52) U.S. Cl.
CPC ............ *G01J 3/0202* (2013.01); *G01J 3/0218* (2013.01); *G01J 3/4406* (2013.01); *G01N 21/05* (2013.01); *G01N 21/645* (2013.01); *G02B 6/262* (2013.01); *G01N 2021/0389* (2013.01); *G01N 2021/6417* (2013.01); *G01N 2021/6482* (2013.01); *G01N 2021/6484* (2013.01);
(Continued)

(58) Field of Classification Search
CPC ...... G01J 3/0202; G01J 3/0218; G01J 3/4406; G01B 6/262; G01N 21/05; G01N 21/645; G01N 2201/0833; G01N 2021/6482

USPC .... 356/244, 246, 432–436, 51, 445; 385/12, 385/37

See application file for complete search history.

(56) References Cited

U.S. PATENT DOCUMENTS

| 4,863,264 A | 9/1989 | Miyake et al. |
| 5,034,194 A | 7/1991 | Miller et al. |
| 5,141,609 A | 8/1992 | Sweedler et al. |

(Continued)

FOREIGN PATENT DOCUMENTS

| EP | 2602611 A2 | 6/2013 |
| JP | S60207038 | 10/1985 |

(Continued)

OTHER PUBLICATIONS

"Schott Deep UV-200 Silicone Adhesive", Schott North America, Inc., Jul. 2013, 1 page.

(Continued)

*Primary Examiner* — Sang Nguyen
(74) *Attorney, Agent, or Firm* — Myers Bigel, P.A.

(57) ABSTRACT

A flow cell for a fluorescence spectrometer includes a flow channel to receive a flow of a liquid sample, an excitation light entrance window to receive excitation light from a light source, and an emission light exit window to transmit fluorescent emission light from the liquid sample in the flow channel from the flow cell. The excitation light entrance window and/or emission light exit window includes a waveguide including: a waveguide core formed of a core material; and a cladding medium surrounding a portion of the waveguide core, wherein the cladding medium has a refractive index less than the refractive index of the core material. The waveguide defines a portion of the flow channel.

27 Claims, 18 Drawing Sheets

(51) Int. Cl.
*G01N 21/64* (2006.01)
*G01N 21/03* (2006.01)

(52) U.S. Cl.
CPC ............... *G01N 2201/0642* (2013.01); *G01N 2201/0826* (2013.01); *G01N 2201/0833* (2013.01)

(56) References Cited

U.S. PATENT DOCUMENTS

| | | | |
|---|---|---|---|
| 5,170,056 A * | 12/1992 | Berard | G01N 21/552 |
| | | | 250/339.11 |
| 5,194,915 A | 3/1993 | Gilby | |
| 5,260,029 A | 11/1993 | Hosoi et al. | |
| 5,270,212 A | 12/1993 | Horiuchi et al. | |
| H1344 H | 8/1994 | Baldauf et al. | |
| 5,408,307 A | 4/1995 | Yamamoto et al. | |
| 5,428,441 A | 6/1995 | Ogino et al. | |
| 5,430,541 A | 7/1995 | Sapp et al. | |
| 5,446,532 A | 8/1995 | Yamazaki | |
| 5,469,251 A | 11/1995 | Kosaka et al. | |
| 5,471,294 A | 11/1995 | Ogino | |
| 5,491,344 A | 2/1996 | Kenny et al. | |
| 5,500,536 A | 3/1996 | Nogami et al. | |
| 5,633,503 A | 5/1997 | Kosaka | |
| 5,644,388 A | 7/1997 | Maekawa et al. | |
| 5,804,453 A * | 9/1998 | Chen | G01N 21/7703 |
| | | | 356/478 |
| 5,874,310 A | 2/1999 | Li et al. | |
| 5,917,584 A | 6/1999 | Li et al. | |
| 6,097,485 A | 8/2000 | Lievan | |
| 6,184,990 B1 | 2/2001 | Amirkhanian et al. | |
| 6,228,652 B1 | 5/2001 | Rodriguez et al. | |
| 6,326,612 B1 | 12/2001 | Elkind et al. | |
| 6,388,746 B1 | 5/2002 | Eriksson et al. | |
| 6,542,231 B1 * | 4/2003 | Garrett | G01N 21/05 |
| | | | 250/227.11 |
| 6,580,507 B2 | 6/2003 | Fry et al. | |
| 6,594,001 B1 | 7/2003 | Yabusaki | |
| 6,603,556 B2 | 8/2003 | Belz et al. | |
| 6,611,334 B1 | 8/2003 | Fernando et al. | |
| 7,161,665 B2 | 1/2007 | Johnson | |
| 7,209,223 B1 | 4/2007 | Hull et al. | |
| 7,251,026 B2 | 7/2007 | Gilby | |
| 7,477,363 B2 | 1/2009 | Nagai | |
| 7,532,313 B2 | 5/2009 | Kitaoka et al. | |
| 7,537,732 B2 | 5/2009 | Gustafson et al. | |
| 7,709,821 B2 | 5/2010 | Casstevens et al. | |
| 7,916,280 B2 | 3/2011 | Ueno et al. | |
| 8,248,604 B2 | 8/2012 | Takeda | |
| 8,405,048 B2 | 3/2013 | Hayashi | |
| 8,441,645 B2 * | 5/2013 | Prabhakar | G01N 21/05 |
| | | | 356/440 |
| 2002/0071123 A1 * | 6/2002 | Miller | G01N 21/05 |
| | | | 356/440 |
| 2005/0161623 A1 | 7/2005 | Carver et al. | |
| 2007/0211244 A1 * | 9/2007 | Hilmer | G01N 30/74 |
| | | | 356/246 |
| 2009/0304551 A1 * | 12/2009 | Mutharasan | G01N 21/05 |
| | | | 422/82.11 |
| 2010/0243916 A1 | 9/2010 | Maurer et al. | |
| 2011/0102792 A1 | 5/2011 | Ozasa | |
| 2011/0140001 A1 | 6/2011 | Piltch et al. | |
| 2011/0207237 A1 * | 8/2011 | Sai | G01N 21/554 |
| | | | 436/518 |
| 2012/0090996 A1 | 4/2012 | Trost et al. | |
| 2013/0063726 A1 * | 3/2013 | Monro | G01N 21/553 |
| | | | 356/445 |
| 2013/0259418 A1 * | 10/2013 | Kontani | G01N 21/553 |
| | | | 385/12 |
| 2013/0286380 A1 * | 10/2013 | Selker | G01J 3/44 |
| | | | 356/51 |
| 2014/0051188 A1 * | 2/2014 | Wang | G01N 21/55 |
| | | | 436/517 |

FOREIGN PATENT DOCUMENTS

JP          H03108641 A       5/1991
WO     WO 2012/144955 A1    10/2012

OTHER PUBLICATIONS

Notification of Transmittal of the International Search Report and the Written Opinion of the International Searching Authority, or the Declaration, in corresponding PCT Application No. PCT/US2015/050143, mailed Mar. 31, 2016 (20 pages).

Invitation to Pay Additional Fee and, Where Applicable, Protest Fee, in corresponding PCT Application No. PCT/US2015/050143, mailed Jan. 19, 2016 (6 pages).

* cited by examiner

FLOW CELL MODULES AND LIQUID SAMPLE ANALYZERS AND METHODS INCLUDING SAME

RELATED APPLICATION(S)

N/A.

FIELD

The present technology relates to liquid sample analyzers and flow cell modules therefor.

BACKGROUND

Liquid sample analyzers of known design include a flow cell, a light source for providing light to the flow cell, a liquid sample source for flowing a liquid sample through the flow cell, and a detector (e.g., a spectrometer) for receiving light from the flow cell (e.g., light transmitted through or emitted by the liquid sample in the flow cell).

SUMMARY

According to embodiments of the technology, a flow cell for a fluorescence spectrometer includes a flow channel to receive a flow of a liquid sample, an excitation light entrance window to receive excitation light from a light source, and an emission light exit window to transmit fluorescent emission light from the liquid sample in the flow channel from the flow cell. The excitation light entrance window and/or emission light exit window includes a waveguide including: a waveguide core formed of a core material; and a cladding medium surrounding a portion of the waveguide core, wherein the cladding medium has a refractive index less than the refractive index of the core material. The waveguide defines a portion of the flow channel.

The core material may be fused silica or quartz.

In some embodiments, the waveguide core defines the portion of the flow channel and contacts the liquid sample in the flow channel.

In some embodiments, the waveguide has total internal reflection.

In some embodiments, the cladding medium is a fluoropolymer.

In some embodiments, the cladding medium is an adhesive.

In some embodiments, the cladding medium is air.

According to some embodiments, the flow cell includes a flow cell body, and the cladding medium is interposed between the flow cell body and the waveguide core. In some embodiments, the flow cell body includes an integral pocket, and the waveguide core and the pocket collectively form a chamber containing the cladding medium. In some embodiments, the cladding medium is an adhesive, and the adhesive bonds the waveguide core to the flow cell body. In some embodiments, the flow cell body is formed of fused silica or quartz.

The flow cell may include a pad of light absorbing material surrounding an end portion of the waveguide core adjacent the flow channel.

In some embodiments, the emission light exit window is oriented at an angle of about 90 degrees with respect to the excitation light entrance window.

According to some embodiments, the waveguide extends from the flow cell to an optical device. In some embodiments, the optical device is at least one of a light source, a monochromator, and a fluorescence detector. In some embodiments, the waveguide is a flexible optical fiber. In some embodiments, the excitation light entrance window and/or emission light exit window includes an optical fiber bundle including a plurality of flexible optical fibers.

According to embodiments of the technology, a flow cell for a fluorescence spectrometer includes a flow cell body, a flow channel to receive a flow of a liquid sample, an excitation light entrance window to receive excitation light from a light source, an emission light exit window to transmit fluorescent emission light from the liquid sample in the flow channel from the flow cell, and at least one mirror integral with the flow cell body. The at least one mirror is positioned: to reflect excitation light that has passed through the liquid sample in the flow channel back into the liquid sample; and/or to reflect emission light emitted from the liquid sample toward the emission light exit window.

According to embodiments of the technology, a flow cell for a fluorescence spectrometer includes a flow channel to receive a flow of a liquid sample, an excitation light entrance window to receive excitation light from a light source, and an emission light exit window to transmit fluorescent emission light from the liquid sample in the flow channel from the flow cell. The emission light exit window is located less than 1.0 mm from the flow channel.

According to embodiments of the technology, a flow cell for a fluorescence spectrometer includes a flow channel to receive a flow of a liquid sample, an excitation light entrance window to receive excitation light from a light source, and an emission light exit window to transmit fluorescent emission light from the liquid sample in the flow channel from the flow cell. The excitation light entrance window is spaced a first distance from the flow channel. The emission light exit window is spaced a second distance from the flow channel. The second distance is less than the first distance.

DETAILED DESCRIPTION

Figure 1:
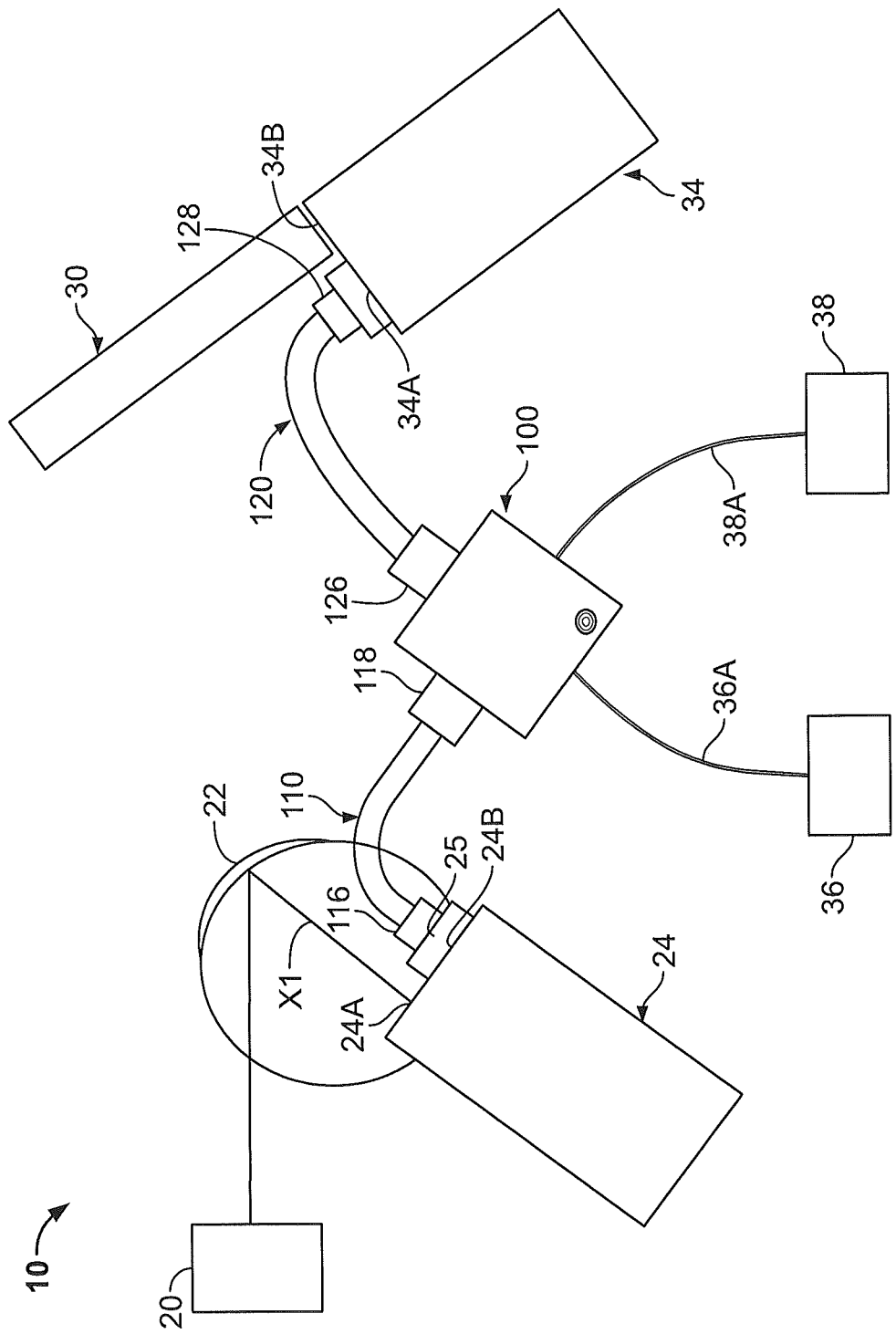
FIG. 1 is a schematic view of a liquid sample analyzer according to embodiments of the technology.

The present technology now will be described more fully hereinafter with reference to the accompanying drawings, in which illustrative embodiments of the technology are shown. In the drawings, the relative sizes of regions or features may be exaggerated for clarity. This technology may, however, be embodied in many different forms and should not be construed as limited to the embodiments set forth herein; rather, these embodiments are provided so that this disclosure will be thorough and complete, and will fully convey the scope of the technology to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present technology.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

The term "monolithic" means an object that is a single, unitary piece formed or composed of a material without joints or seams.

With reference to FIGS. 1-22, a liquid sample analyzer 10 including a flow cell assembly or module 100 according to embodiments of the technology is shown therein. The liquid sample analyzer 10 further includes a remote radiation or light source 20, a mirror 22, an excitation monochromator 24, an emission monochromator 34, a remote sensing device or detector 30, a remote liquid sample source 36, a remote liquid sample receiver 38, and liquid tubing 36A, 38A. Some or all of these components may be housed in a cabinet, for example. The flow cell module 100 includes a flow cell 150, a fiber optic input cable 110, and a fiber optic output cable 120. The cables 110 and 120 provide direct fiber optic interfaces between the flow cell 150 and the monochromator 24 and between the flow cell 150 and the monochromator 34. According to some embodiments, the liquid sample analyzer 10 is a fluorescence spectrometer.

Generally, the liquid sample analyzer 10 operates as a liquid chromatograph that induces fluorescence in a liquid sample and analyzes the emitted fluorescence. A liquid sample is supplied to the flow cell 150 from the liquid sample source 36 through the tubing 36A, and may be flowed through the flow cell 150 and the tubing 38A to the liquid sample receiver 38. Light generated by the light source 20 is directed onto an entrance port or slit 24A of the excitation monochromator 24. The excitation monochromator 24 selects an excitation wavelength and the incoming light of the selected wavelength is transmitted to illuminate an exit port or slit 24B of the excitation monochromator 24. The fiber optic input cable 110 optically connects the exit slit 24B to the flow cell 150 and transmits excitation light of the selected wavelength to the flow cell 150. The beam of excitation light transmitted to the flow cell 150 bombards the liquid sample therein, causing components of the liquid sample to correspondingly emit light (fluoresce). The fluorescent light is collected by the fiber optic output cable 120 and transmitted through the cable 120 to an entrance port or slit 34A of the emission monochromator 34. The emission monochromator 34 selects an emissions wavelength and the incoming light of the selected wavelength is transmitted to illuminate an exit port or slit 34B of the emission monochromator 34. The sensing device 30 is directly or indirectly optically connected to the exit slit 34B.

The light from the excitation light source 20 thus passes through the excitation monochromator 24 and strikes the liquid sample. A proportion of the incident light is absorbed by the sample, and some of the molecules of the sample fluoresce. The fluorescent light is emitted in all directions and a portion thereof passes from the flow cell 150 and through the emission monochromator 34 and reaches the sensing device 30. The entrance end of the fiber optic output cable 120 is located at 90 degrees relative to the incident (excitation) light beam in order to minimize the risk of excitation light reaching the sensing device 30.

The light source 20 can be any suitable source of radiation or light for spectroscopic analysis. The light source 20 includes a lamp contained in a housing. According to some embodiments, the lamp is a Xenon lamp. In some embodiments, the lamp is a Xenon lamp with a wattage in the range of from about 10 to 150 watts. In some embodiments, the lamp is pulsed at a frequency in the range of from about 20 to 1000 Hz with a pulse width in the range of from about 2 to 20 microseconds.

The mirror 22 can be any suitable radiation reflective mirror configured and positioned to direct light from the light source 20 onto the entrance slit 24A of the monochromator 24. According to some embodiments, the mirror 22 focuses the light from the light source 20 onto the entrance slit 24A. According to some embodiments, the mirror 22 is a toroidal mirror. A baffle may be provided between the light source 20 and the mirror 22 to reduce possible stray light.

The excitation monochromator 24 is used to select the excitation wavelength used in the analysis method, procedure or session. The excitation monochromator 24 can be any suitable monochromator configured to receive an input light beam and transmit a selected band of wavelengths of light from the wider range of wavelengths in the input light beam. The input light beam from the mirror 22 is received through the slit 24A and the selected light is transmitted out through the slit 24B.

An interface connector 25 is secured to the housing of the monochromator 24 around the output slit 24B. The connector 25 includes a socket 25A aligned with the slit 24B, locator feature 25B (i.e., opposed flat side walls), and a retention screw 25C.

The excitation monochromator 24 may accomplish the wavelength selection using optical dispersion by a prism or diffraction using a diffraction grating. In some embodiments, the excitation monochromator 24 employs a concave holographic diffraction grating. The input light is dispersed by the prism or diffraction grating into a spectrum that illuminates the output slit 24B. The excitation monochromator 24 will typically include a motor (e.g., a stepper motor) or other actuator operative to mechanical adjust or scan the selected wavelength bands that are directed onto the output slit 24B.

Figure 2:
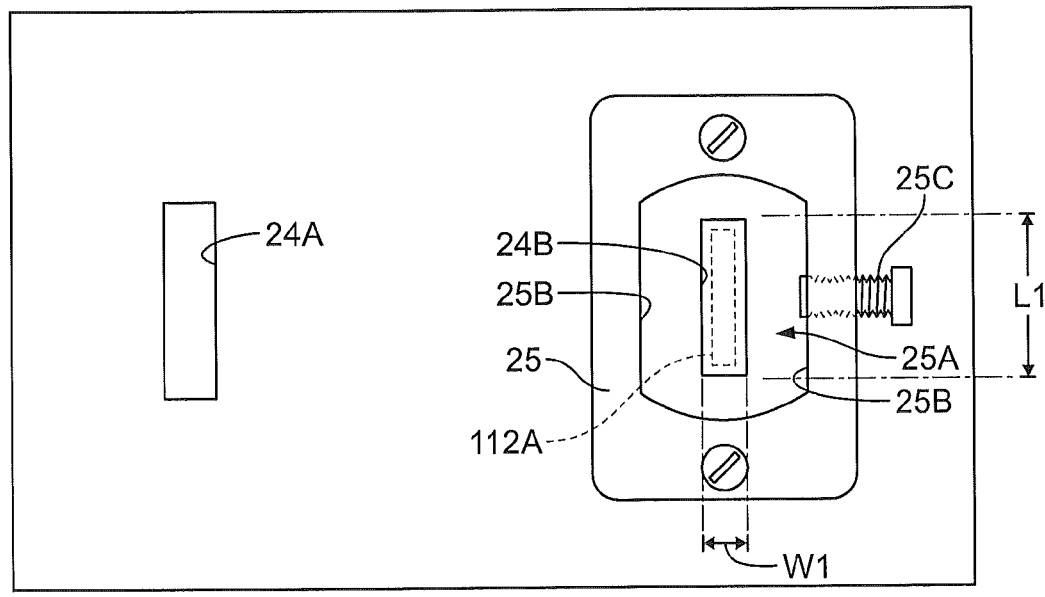
FIG. 2 is an end view of an excitation monochromator forming a part of the liquid sample analyzer of FIG. 1.

The output slit 24B has a length L1 and a width W1 (FIG. 2). In some embodiments, the length L1 is in the range of from about 5 to 20 mm and the width W1 is in the range of from about 0.5 to 5 mm. In some embodiments, the output slit 24B has a total area in the range of from about 2.5 to 100 mm$^2$. In some embodiments, the output slit 24B is substantially rectangular.

The emission monochromator 34 is used to select the emissions wavelength used in the analysis method, procedure or session. The emission monochromator 34 can be any suitable monochromator configured to receive an input light beam and transmit a selected band of wavelengths of light from the wider range of wavelengths in the input light beam. The input light beam from the cable 120 is received through the slit 34A and the selected light is transmitted out from the emission monochromator 34 through the slit 34B.

An interface connector 35 is secured to the housing of the monochromator 34 around the input slit 34A. The connector 35 includes a socket 35A aligned with the slit 34A, locator features 35B, and a retention screw 35C.

The emission monochromator 34 may accomplish the wavelength selection using optical dispersion by a prism or diffraction using a diffraction grating. In some embodiments, the emission monochromator 34 employs a concave holographic diffraction grating. The input light is dispersed by the prism or diffraction grating into a spectrum that illuminates the output slit 34B. The emission monochromator 34 will typically include a motor (e.g., a stepper motor) or other actuator operative to mechanical adjust or scan the selected wavelength bands that are directed onto the output slit 34B.

Figure 3:
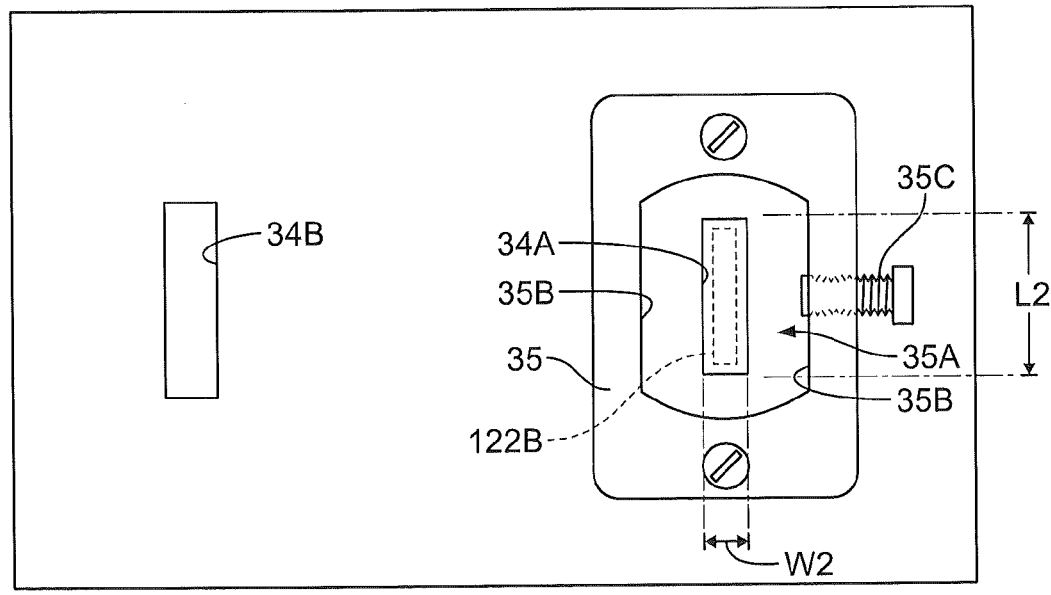
FIG. 3 is an end view of an emission monochromator forming a part of the liquid sample analyzer of FIG. 1.
Figure 4:
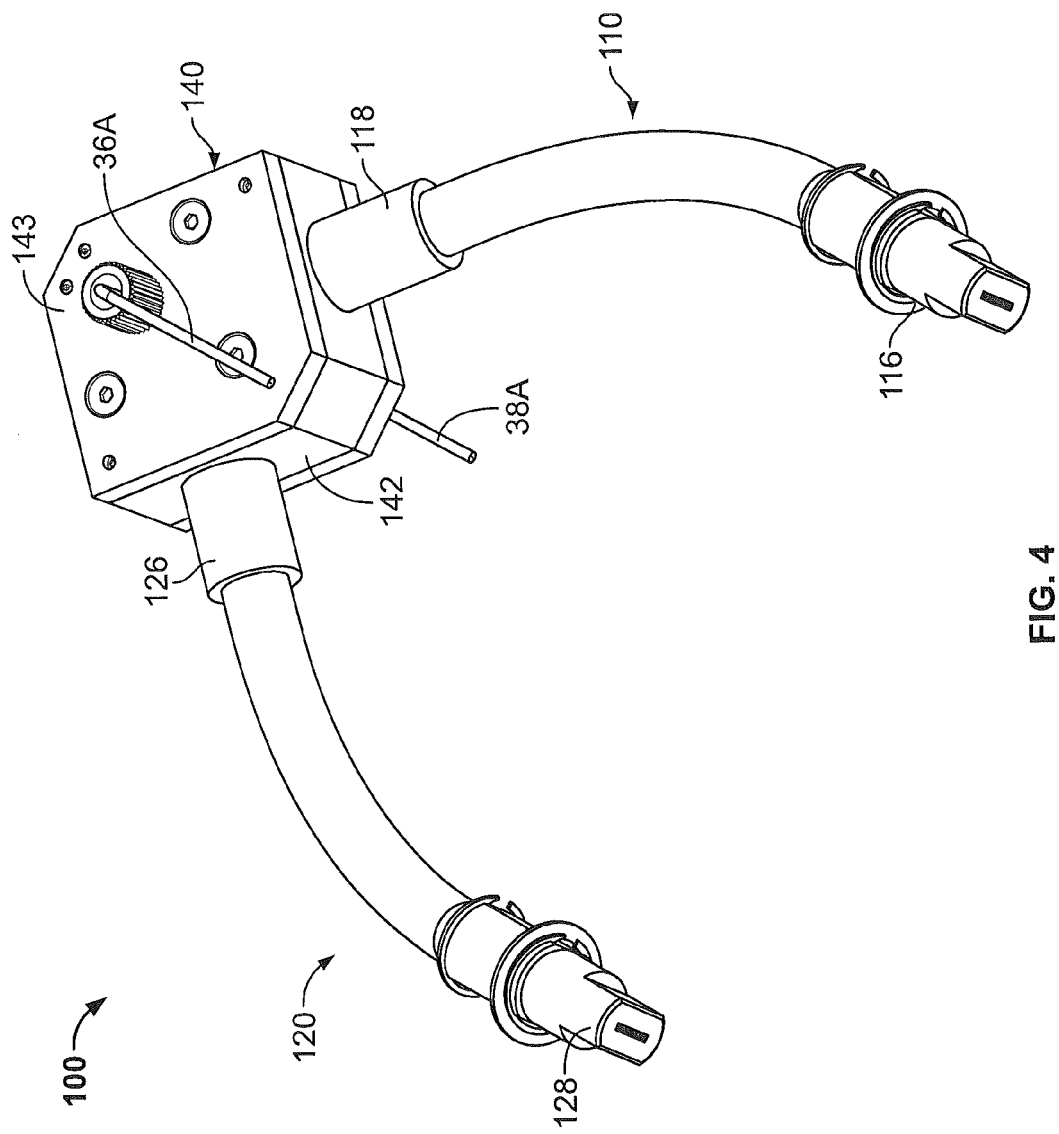
FIG. 4 is a perspective view of a flow cell module forming a part of the liquid sample analyzer of FIG. 1.
Figure 5:
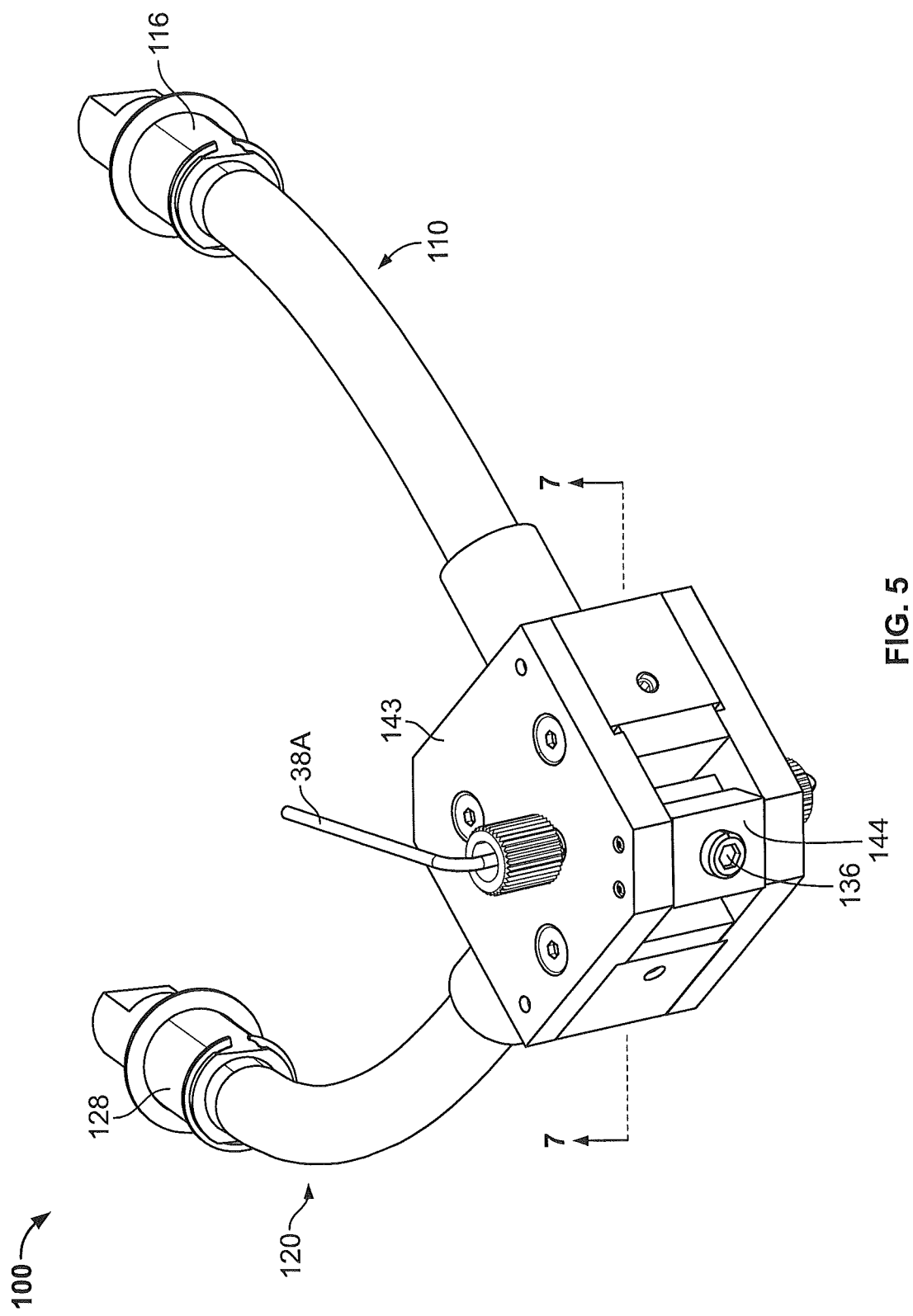
FIG. 5 is an opposing perspective view of the flow cell module of FIG. 4.
Figure 6:
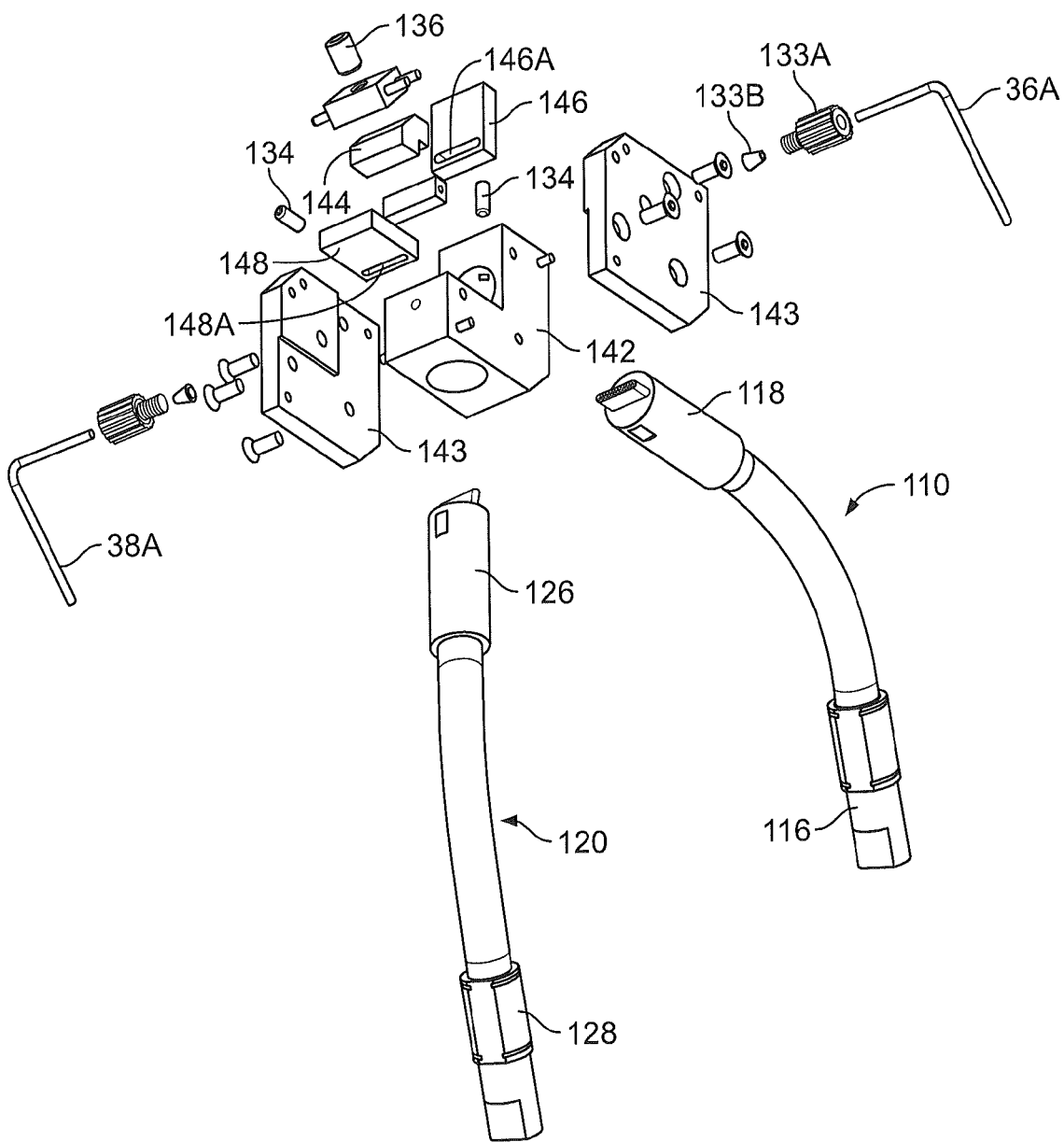
FIG. 6 is an exploded, perspective view of the flow cell module of FIG. 4.

The input slit 34A has a length L2 and a width W2 (FIG. 3). In some embodiments, the length L2 is in the range of from about 5 to 20 mm and the width W2 is in the range of from about 0.5 to 5 mm. In some embodiments, the input slit 34A has a total area in the range of from about 2.5 to 100 mm$^2$. In some embodiments, the input slit 34A is substantially rectangular.

The sensing device 30 may be any suitable sensing device or detector for spectroscopic analysis. According to some embodiments, the detector 30 is a spectrometer. According to some embodiments, the detector 30 is a spectrometer including a photomultiplier tube or a photodiode array (PDA). In some embodiments, a long pass filter is interposed between the exit slit 34B and the input of the detector 30.

The liquid sample source 36 may be any suitable source including a supply of the sample to be analyzed. In some embodiments, the liquid sample includes a sample component or analyte of interest in a solvent. According to some embodiments, the solvent is aqueous. The liquid sample receiver 38 may be a waste receptacle or a down line process.

The flow cell module 100 includes a flow cell unit or assembly 150, a connectorized radiation input or source optical fiber cable 110, a connectorized radiation output or detector optical fiber cable 120, a liquid sample feed capillary tube 36A, a liquid sample exit capillary tube 38A, and a flow cell frame assembly 140.

The liquid sample source 36 and the liquid sample receiver 38 are fluidly connected to the flow cell 150 by the tubes 36A and 38A, respectively. According to some embodiments, at least one of the liquid sample source 36 and the liquid sample receiver 38 is provided with a pump to generate a forced flow of the liquid sample through the tubes 36A, 38A and the flow cell unit 150. According to some embodiments, the tubes 36A, 38A are flexible. In some embodiments, the tubes 36A, 38A are capillary tubes. In some embodiments, the tubes 36A, 38A are formed of fused silica or quartz.

With reference to FIGS. 11-14, the input cable 110 has an input end 110A and an output end 110B. The cable 110 includes a bundle 112 of a plurality of flexible optical fibers 113, a protective jacket 114, an input termination or connector 116, and an output termination or connector 118. The fiber bundle 112 includes an input end section 112D, an output end section 112E, and an intermediate or connecting section 112F. Each fiber 113 has an optical fiber end face 113A on the cable end 110A and an optical fiber end face 113B on the cable end 110B. The fiber end faces 113A collectively form a fiber bundle input end face 112A. The fiber end faces 113B collectively form a fiber bundle output end face 112B. In some embodiments, the cable 110 further includes a flexible supporting fiber 113X that is not an optical fiber (e.g., a polymer fiber such as aramid) to fill out the array geometry.

Each of the optical fibers 113 may be an optical fiber including a solid glass core and a solid glass cladding and may be covered in a protective coating (e.g., acrylate polymer or polyimide). In some embodiments, the core and cladding layers are selected to have a difference in refractive index that provides total internal reflection (TIR) in the core.

In some embodiments, the fibers 113 each have a cross-sectional diameter in the range of from about 150 to 300 micrometers.

According to some embodiments, the bundle 112 includes at least 75 optical fibers 113 extending fully and continuously from end face 112A to end face 112B, in some embodiments at least 85 such fibers 113, and in some embodiments, from about 70 to 120 such fibers 113.

In some embodiments, the interior cross-section of the jacket 114 is greater than the collective outer diameter of the bundle 112 so that an excess volume or space is provided in the jacket 114 for movement and flexing of the connecting section 112F. In some embodiments, additional protective tubing or layers may be provided about the bundle 112.

The input connector 116 has the form of a ferrule and has a connector body 116A and an end face 116C. The connector body 116A is provided with locator features 116F in the form of opposed flat sides. A passage extends through the body 116A and terminates at an end slot 116D. The end section 112D is secured in the passage by adhesive or potting such that the fiber bundle end face 112A is exposed and lies substantially flush with the end face 116C at the end slot 116D.

The output connector 118 likewise has the form of a ferrule and has a connector body 118A, a connector extension 118B, and an extension end face 118C. A passage 118E extends through the body 118A and extension 118B and terminates at an end slot 118D. The end section 112E is secured in the passage 118E by adhesive or potting 115 such that the fiber bundle end face 112B lies flush with the extension end face 118C at the end slot 118D.

As discussed in more detail below, the fiber bundle end section 112D and the fiber bundle end face 112A are shaped and configured to define an array 111A of a first prescribed or selected configuration. Similarly, the fiber bundle end section 112E and the fiber bundle end face 112B are shaped and configured to define an array 111B of a second prescribed or selected configuration. The intermediate fiber bundle section 112F is further shaped and configured or permitted to assume a configuration that may differ from those of the sections 112D and 112E. For example, the section 112F may assume a substantially round cross-sectional shape or other shape generally conforming to the inner diameter of the jacket 114.

According to some embodiments, the geometric configuration and dimensions of the array 111A are different than the geometric configuration and dimensions of the array 111B. According to some embodiments, the geometric configuration and dimensions of the array 111A are different than the geometric configuration and dimensions of the array 111B while the number of fiber end faces 113A in the array 111A is the same as the number of fiber end faces 113B in the array 111B.

Figure 13:
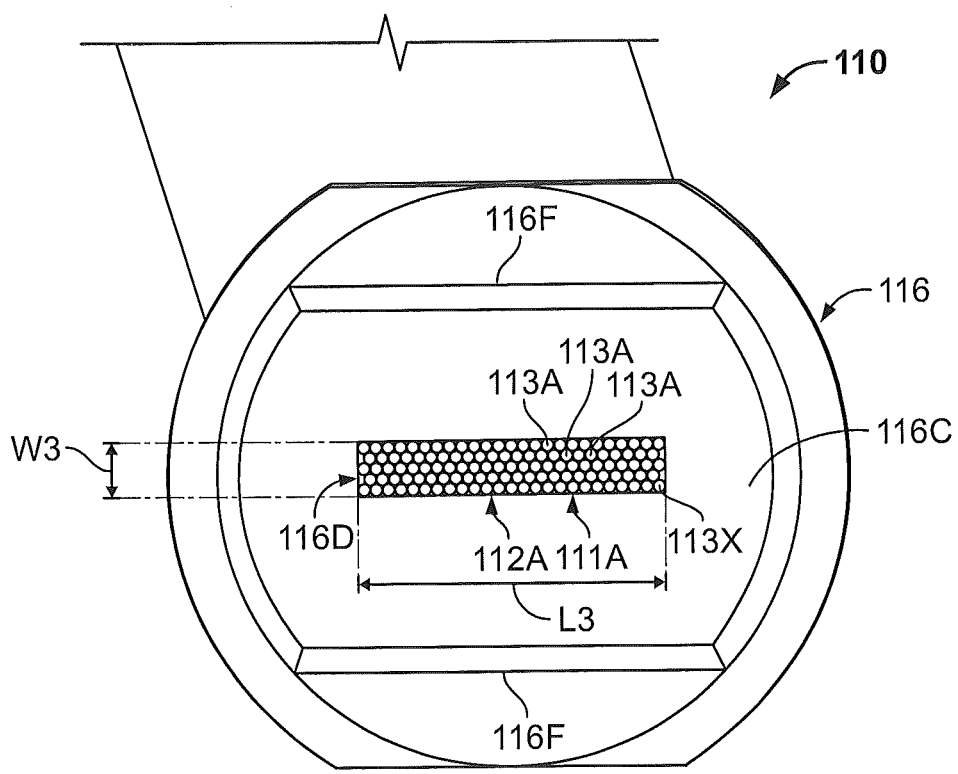
FIG. 13 is a first end view of the input cable of FIG. 11.

The input end face 112A has a length L3 and a width W3 (FIG. 13). In some embodiments, the length L3 is in the range of from about 3 to 10 mm and the width W3 is in the range of from about 0.5 to 2 mm. In some embodiments, the input end face 112A has a total area in the range of from about 1.5 to 20 mm². In some embodiments, the input end face 112A is substantially rectangular.

Figure 14:
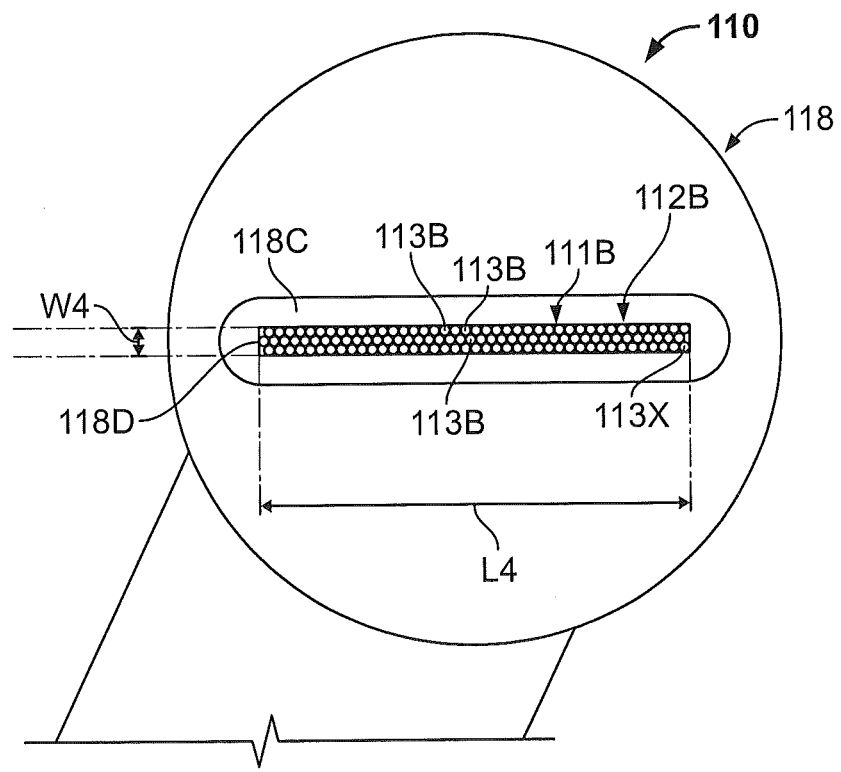
FIG. 14 is an opposing end view of the input cable of FIG. 11.
Figure 15:
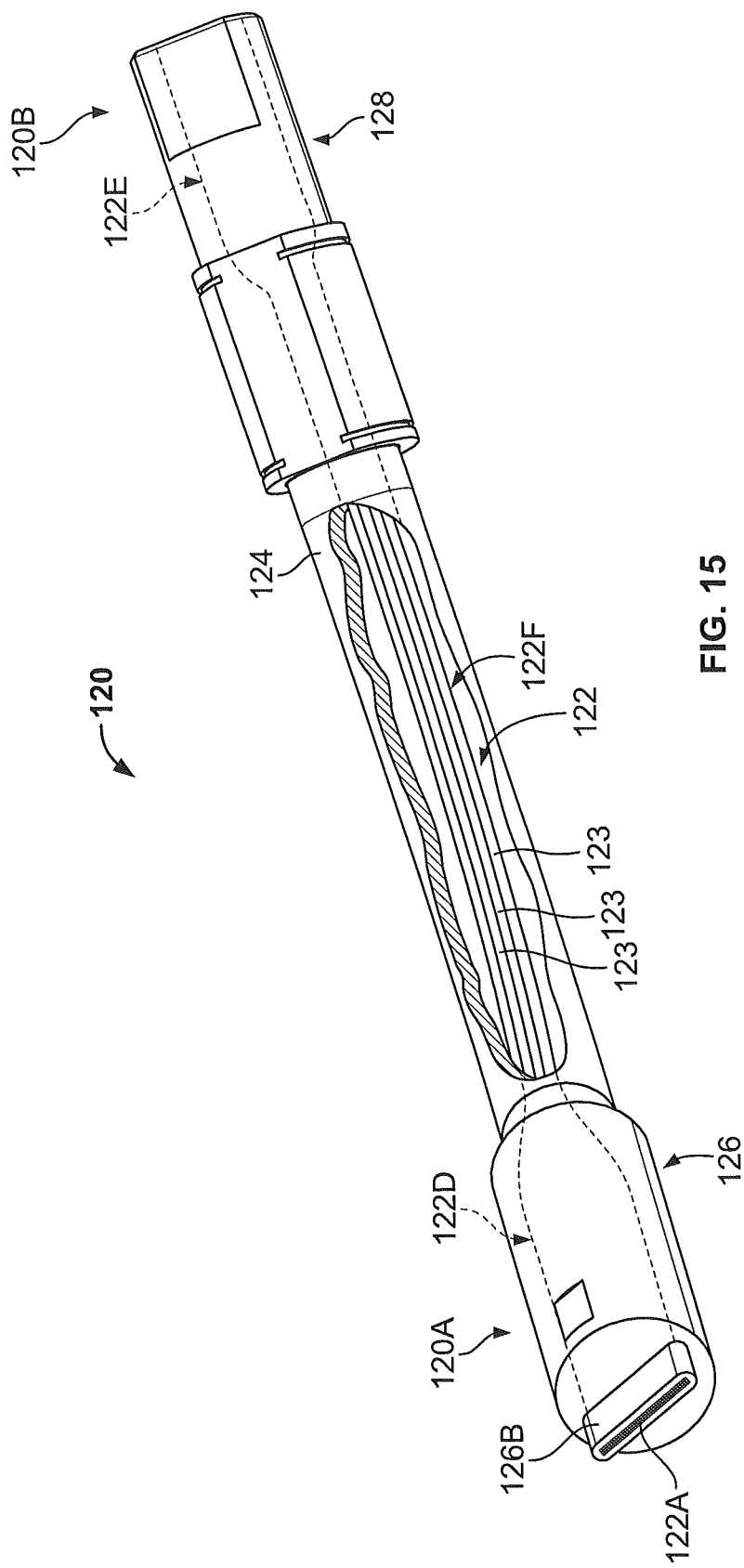
FIG. 15 is a fragmentary, perspective view of an output cable forming a part of the flow cell module of FIG. 4.
Figure 16:
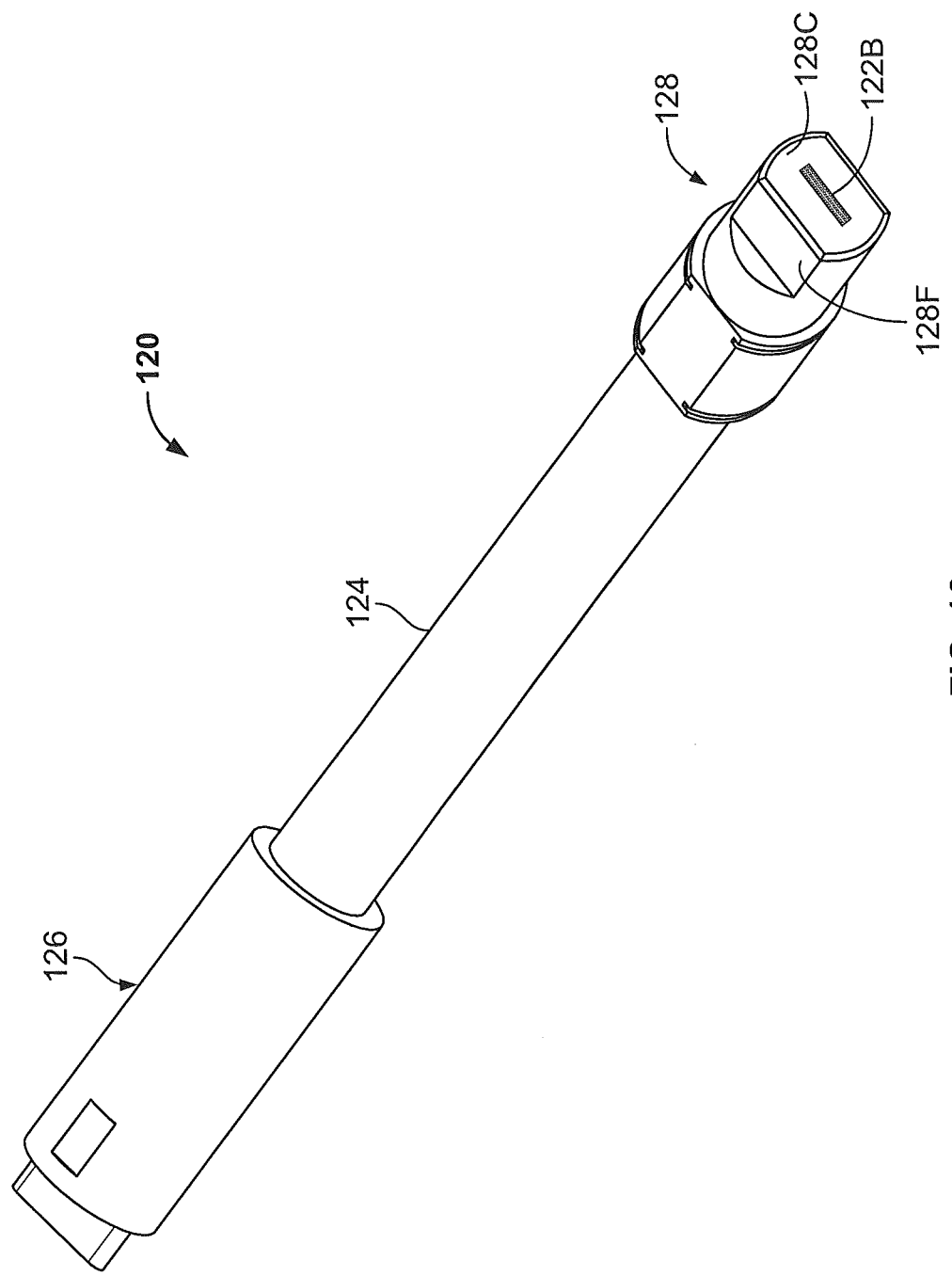
FIG. 16 is a perspective view of the output cable of FIG. 15.

The output end face 112B has a length L4 and a width W4 (FIG. 14). In some embodiments, the length L4 is in the range of from about 3 to 10 mm and the width W4 is in the range of from about 0.5 to 2 mm. In some embodiments, the output end face 112B has a total area in the range of from about 1.5 to 20 mm². In some embodiments, the output end face 112B is substantially rectangular.

With reference to FIGS. 15-18, the output cable 120 has an input end 120A and an output end 120B. The cable 120 includes a bundle 122 of a plurality of flexible optical fibers 123, a protective jacket 124, an input termination or connector 126, and an output termination or connector 128. The fiber bundle 122 includes a input end section 122D, an output end section 122E, and an intermediate or connecting section 122F. Each fiber 123 has an optical fiber end face 123A on the cable end 120A and an optical fiber end face 123B on the cable end 120B. The fiber end faces 123A collectively form a fiber bundle end face 122A. The fiber end faces 123B collectively form a fiber bundle end face 122B. In some embodiments, the cable 120 further includes a flexible supporting fiber 123X that is not an optical fiber to fill out the array geometry.

Each of the optical fibers 123 may be an optical fiber including a solid glass core and a solid glass cladding and may be covered in a protective coating (e.g., acrylate polymer or polyimide). In some embodiments, the core and cladding layers are selected to have a difference in refractive index that provides total internal reflection (TIR). In some embodiments, the fibers 123 each have a cross-sectional diameter in the range of from about 150 to 250 micrometers.

According to some embodiments, the bundle 122 includes at least 50 optical fibers 123 extending fully and continuously from end face 122A to end face 122B, in some embodiments at least 80 such fibers 123, and in some embodiments, from about 50 to 100 such fibers 123.

In some embodiments, the interior cross-section of the jacket 124 is greater than the collective outer diameter of the bundle 122 so that an excess volume or space is provided in the jacket for movement and flexing of the connecting section 122F. In some embodiments, additional protective tubing or layers may be provided about the bundle 122.

The input connector 126 has the form of a ferrule and has a connector body 126A, a connector extension 126B, and an extension end face 126C. A passage 126E extends through the body 126A and extension 126B and terminates at an end slot 126D. The fiber bundle end section 122D is secured in the passage 126E by adhesive or potting 115 such that the fiber bundle end face 122A is exposed and lies substantially flush with the extension end face 126C at the end slot 126D.

The output connector 128 likewise has the form of a ferrule and has a connector body 128A and an end face 128C. The connector body 128A is provided with locator features 128F in the form of opposed flat sides. A passage extends through the body 128A and terminates at an end slot 128D. The fiber bundle end section 122E is secured in the passage by adhesive or potting such that the fiber bundle end face 122B lies flush with the extension end face 128C at the end slot 128D.

As discussed in more detail below, the fiber bundle end section 122D and the fiber bundle end face 122A are shaped and configured to define an array 121A of a first prescribed or selected configuration. Similarly, the fiber bundle end section 122E and the fiber bundle end face 122B are shaped and configured to define an array 121B of a second prescribed or selected configuration. The intermediate fiber bundle section 122F is further shaped and configured or permitted to assume a configuration that may differ from those of the sections 122D and 122E. For example, the section 122F may assume a substantially round cross-sectional shape or other shape generally conforming to the inner diameter of the jacket 124.

According to some embodiments, the geometric configuration and dimensions of the array 121A are different than the geometric configuration and dimensions of the array 121B. According to some embodiments, the geometric configuration and dimensions of the array 121A are different than the geometric configuration and dimensions of the array 121B while the number of fiber end faces 123A in the array 121A is the same as the number of fiber end faces 123B in the array 121B.

Figure 17:
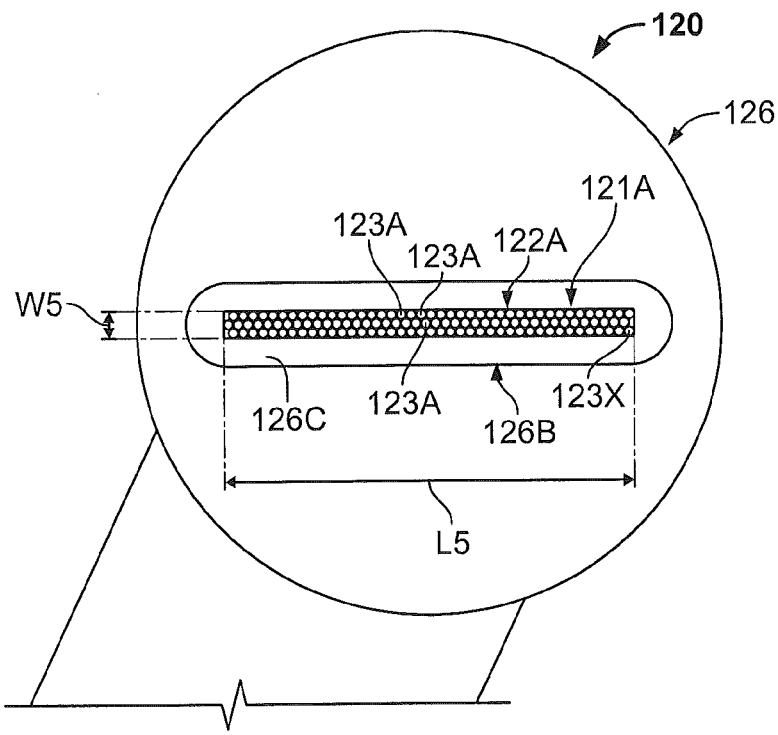
FIG. 17 is a first end view of the output cable of FIG. 15.

The input end face 122A has a length L5 and a width W5 (FIG. 17). In some embodiments, the length L5 is in the range of from about 3 to 10 mm and the width W5 is in the range of from about 0.5 to 2 mm. In some embodiments, the input end face 122A has a total area in the range of from about 1.5 to 20 mm$^2$. In some embodiments, the input end face 122A is substantially rectangular.

Figure 18:
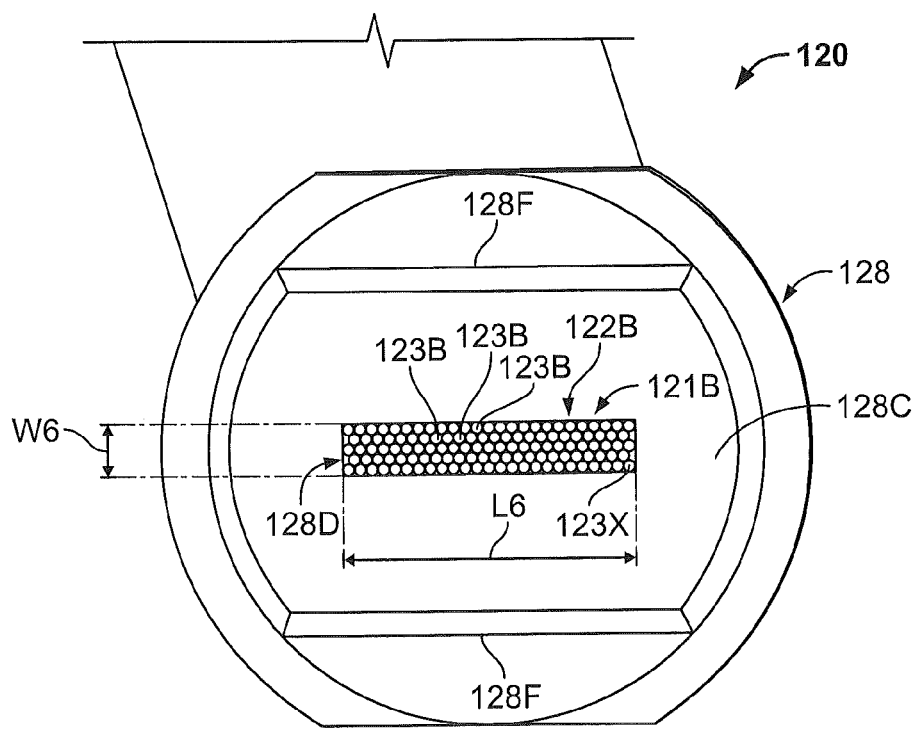
FIG. 18 is an opposing end view of the output cable of FIG. 15.
Figure 19:
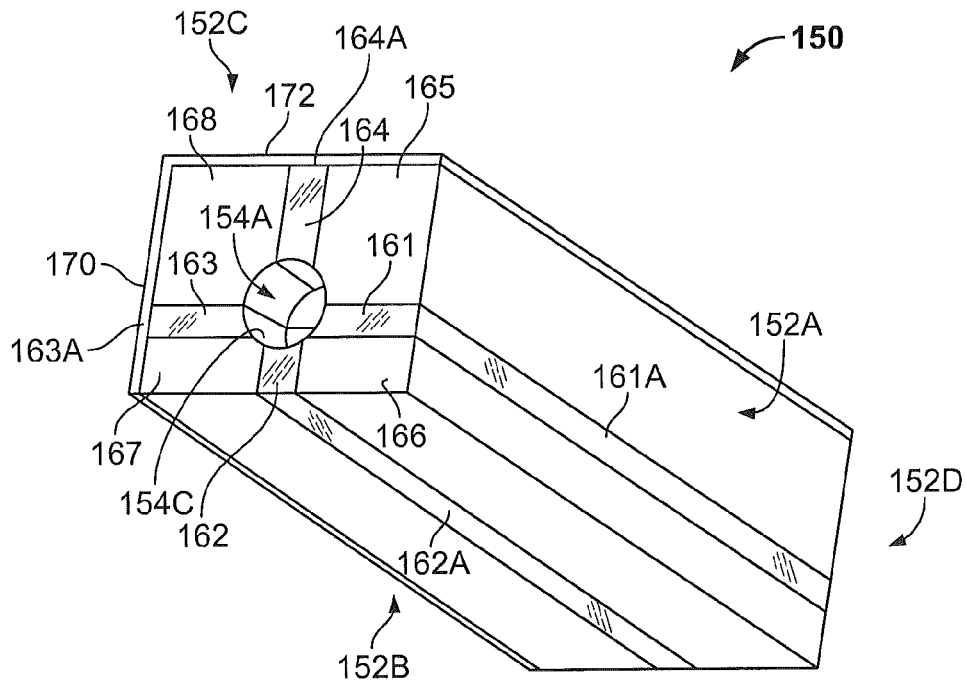
FIG. 19 is a perspective view of a flow cell forming a part of the flow cell module of FIG. 4.
Figure 20:
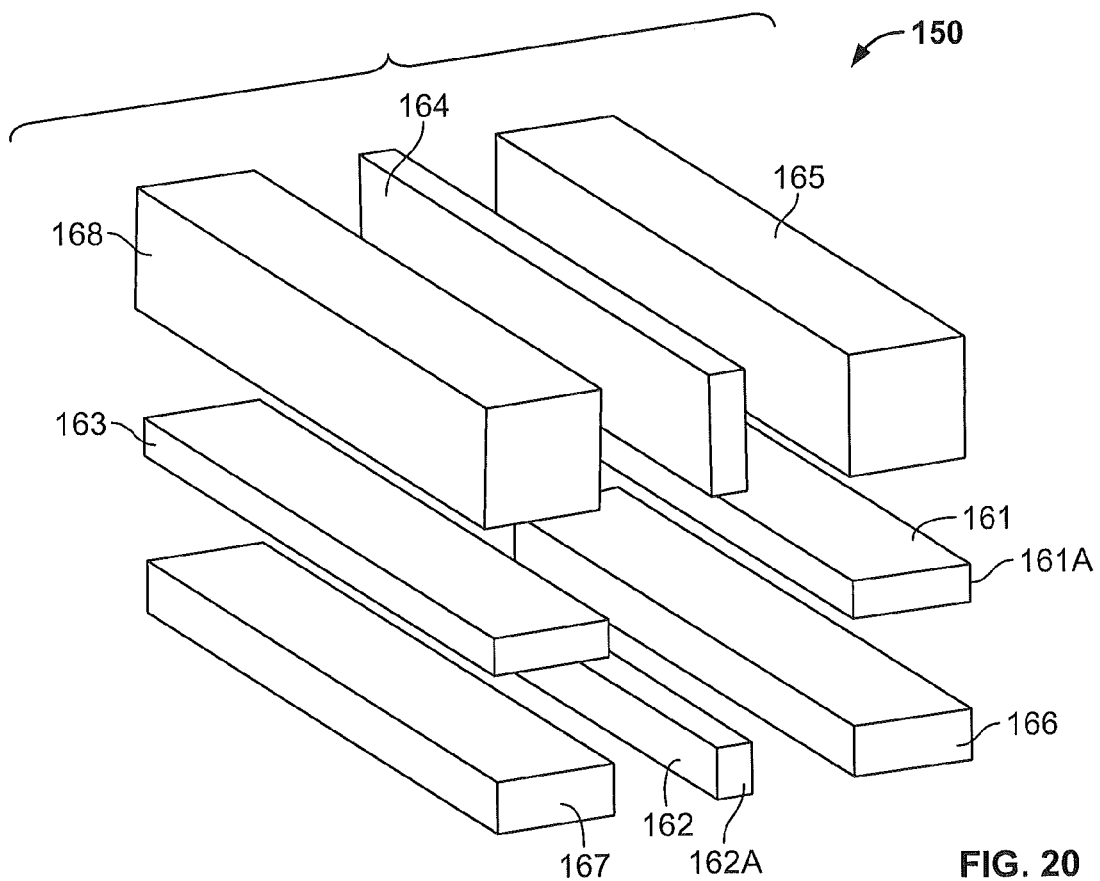
FIG. 20 is an exploded, perspective view of the flow cell of FIG. 19.

The output end face 122B has a length L6 and a width W6 (FIG. 18). In some embodiments, the length L6 is in the range of from about 3 to 10 mm and the width W6 is in the range of from about 0.5 to 2 mm. In some embodiments, the output end face 122B has a total area in the range of from about 1.5 to 20 mm$^2$. In some embodiments, the output end face 122B is substantially rectangular.

The flow cell 150 is seated in and supported by the frame assembly 140. The frame assembly 140 includes a frame body 142, opposed side plates 143, a clamp block 144, an input side spacer 146 and an output side spacer 148. The flow cell 150 is seated in the cavity defined by the components 142, 143 and captured therein by the clamp block 144, which is adjustable by means of a bolt 136. A connector bore 142A is defined in the frame body 142 to receive the connector 118. A connector bore 142B is also defined in the frame body 142 to receive the connector 126 and extends at a 90 degree angle to the connector bore 142A. The spacers 146 and 148 include slots 146A and 148A, respectively, that are aligned with the bores 142A and 142B, respectively.

With reference to FIGS. 10 and 19-22, the flow cell 150 has a light input side 152A, a light output side 152B, a liquid entrance end 152C, and a liquid exit end 152D. The flow cell 150 includes four waveguide blocks 161, 162, 163, 164 and four corner blocks 165, 166, 167, 168 interposed between the waveguide blocks 161-164. The side faces 169 of the waveguide blocks 161-164 are bonded to the immediately adjacent interfacing side surfaces of the corner blocks 165-168. In some embodiments the side faces 169 are bonded to the corner blocks 165-168 by contact bonding wherein the materials of the interfacing surfaces diffuse into one another. Reflector or mirror layers 170, 172 cover the waveguide blocks 163 and 164 on the sides of the flow cell 150 opposite the sides 152A and 152B, respectively.

The outer end faces 161A-164A of the waveguide blocks 161-164 form portions of the outer sides of the flow cell 150. The inner end faces 161B-164B of the waveguide blocks 161-164 abut at their corners to collective define and form a liquid channel 154. The waveguide blocks 161, 162, 163, 164 serves as waveguides and define respective light channels 174A, 174B, 174C, and 174D which extend from their respective outer end faces 161A-164A and intersect at the channel 154. The channel 154 has an entrance opening 154A and an opposed exit opening 154B.

The light channels 174A, 174B, 174C, and 174D have light channel axes A-A, B-B, C-C and D-D, respectively, extending from their outer faces to the liquid channel 154. The light channel axis A-A extends transversely to the light channel axis B-B. In some embodiments and as shown, the light channel axis A-A extends substantially perpendicularly (i.e., at a substantially 90 degree angle) to the light channel axis B-B. The light channel axis C-C extends collinearly with the light channel axis A-A, and the light channel axis D-D extends collinearly with the light channel axis B-B.

Tube bores 154C are defined in the ends 152C, 152D to receive, position and securely connect the tubes 36A, 38A in fluid communication with the openings 154A, 154B using the fittings 133A and seals 133B.

The waveguide blocks 161-164 are formed of a light transmissive or clear material. The waveguide blocks 161-164 have a light transmissivity of at least 50 percent and, in some embodiments, at least 90 percent. In some embodiments, the waveguide blocks 161-164 are formed of quartz, fused silica or SUPRASIL™ synthetic fused silica to serve as optical waveguides or light pipes for the incident and emitted light. In some embodiments, each of the waveguide blocks 161-164 is monolithic.

According to some embodiments, the side faces 161A-164A of the waveguide blocks 161-164 have an optically polished finish (with a surface roughness less than 1 nm) to reduce light scattering. According to some embodiments, the outer end faces 161A-164A and the inner end faces 161B-164B have an optically polished finish (with a surface roughness less than 5 nm) to reduce light scattering.

According to some embodiments, the corner blocks 165-168 are formed of a light absorbing material to reduce scattered light in the flow cell 150. In some embodiments, the corner blocks 165-168 are formed of blackened (e.g., carbon-filled) quartz, fused silica or SUPRASIL™ synthetic fused silica. In some embodiments, each of the corner blocks 165-168 is monolithic.

The mirror layers 170, 172 are directly bonded to the outer end faces 163A, 164A of the waveguide blocks so that the mirror layers 170, 172 are integral components of the flow cell 150. The mirror layers 170, 172 may be formed of any suitable material(s). In some embodiments, each mirror layer 170, 172 includes a metallic layer and, in some embodiments includes an protective overcoat layer coating the metallic layer on at least the side opposite the associated waveguide block 163 or 164. In some embodiments, each mirror layer 170, 172 is a protected aluminum layer and, in some embodiments, the overcoat layer is silicon dioxide. A protective opaque layer (e.g., a black enamel) may be provided on the outer surfaces of the mirror layers 170, 172. In some embodiments, each mirror layer 170, 172 has a thickness in the range of from about 10 to 100 micrometers. The mirror layers 170, 172 may be applied to blocks 163A and 164A by vapor deposition, for example.

Figure 21:
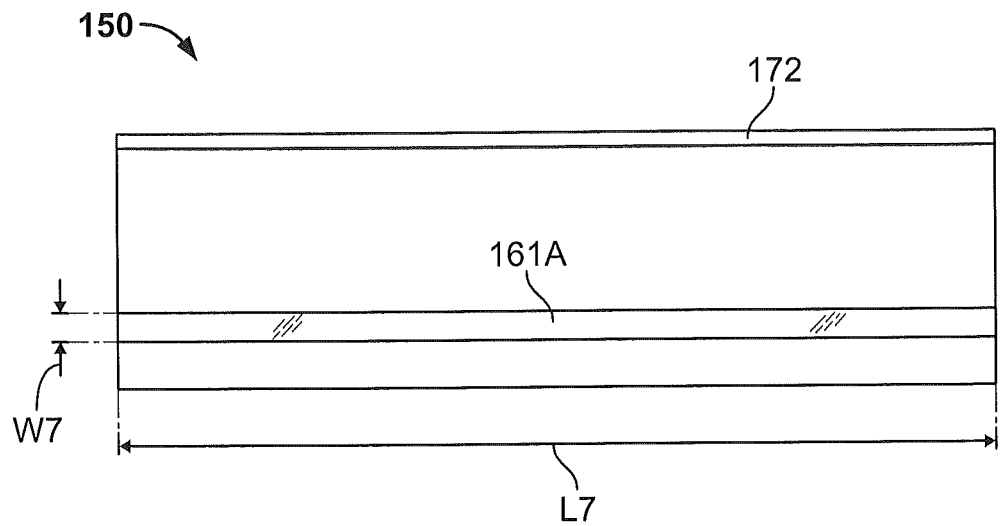
FIG. 21 is a front view of the flow cell of FIG. 19.

The waveguide end face 161A forms a light input port or excitation light entrance window of the flow cell 150 and has a length L7 and a width W7 (FIG. 21). In some embodiments, the length L7 is in the range of from about 3 to 10 mm and the width W7 is in the range of from about 0.5 to 2 mm. In some embodiments, the end face 161A has a total area in the range of from about 1.5 to 20 mm$^2$. In some embodiments, the end face 161A is substantially rectangular.

Figure 22:
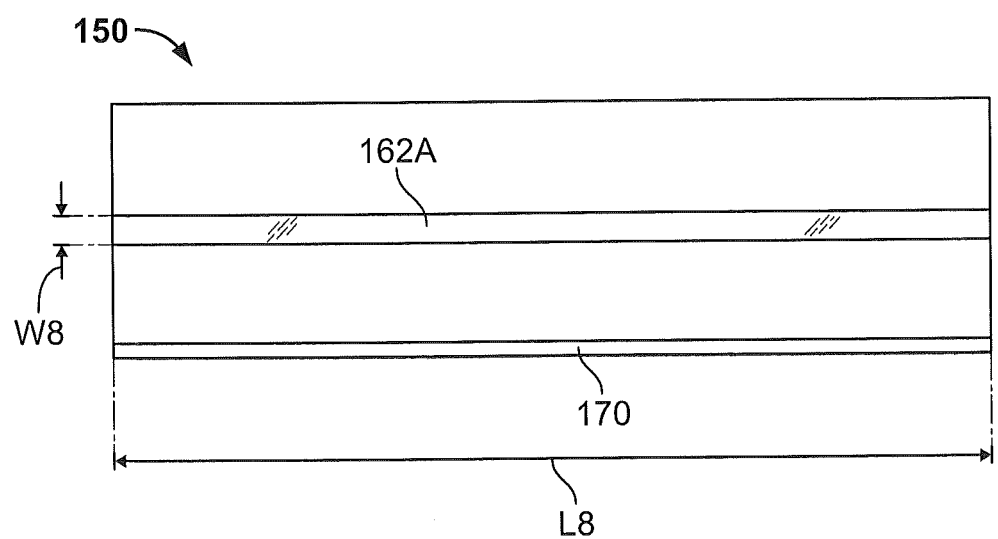
FIG. 22 is a bottom view of the flow cell of FIG. 19.

The waveguide end face 162A forms a light output port or emission light exit window of the flow cell 150 and has a length L8 and a width W8 (FIG. 22). In some embodiments, the length L8 is in the range of from about 3 to 10 mm and the width W8 is in the range of from about 0.5 to 2 mm. In some embodiments, the end face 162A has a total area in the range of from about 1.5 to 20 mm$^2$. In some embodiments, the end face 162A is substantially rectangular. In some embodiments, the output end face 162A has substantially the same size and shape as the input end face 161A.

Figure 10:
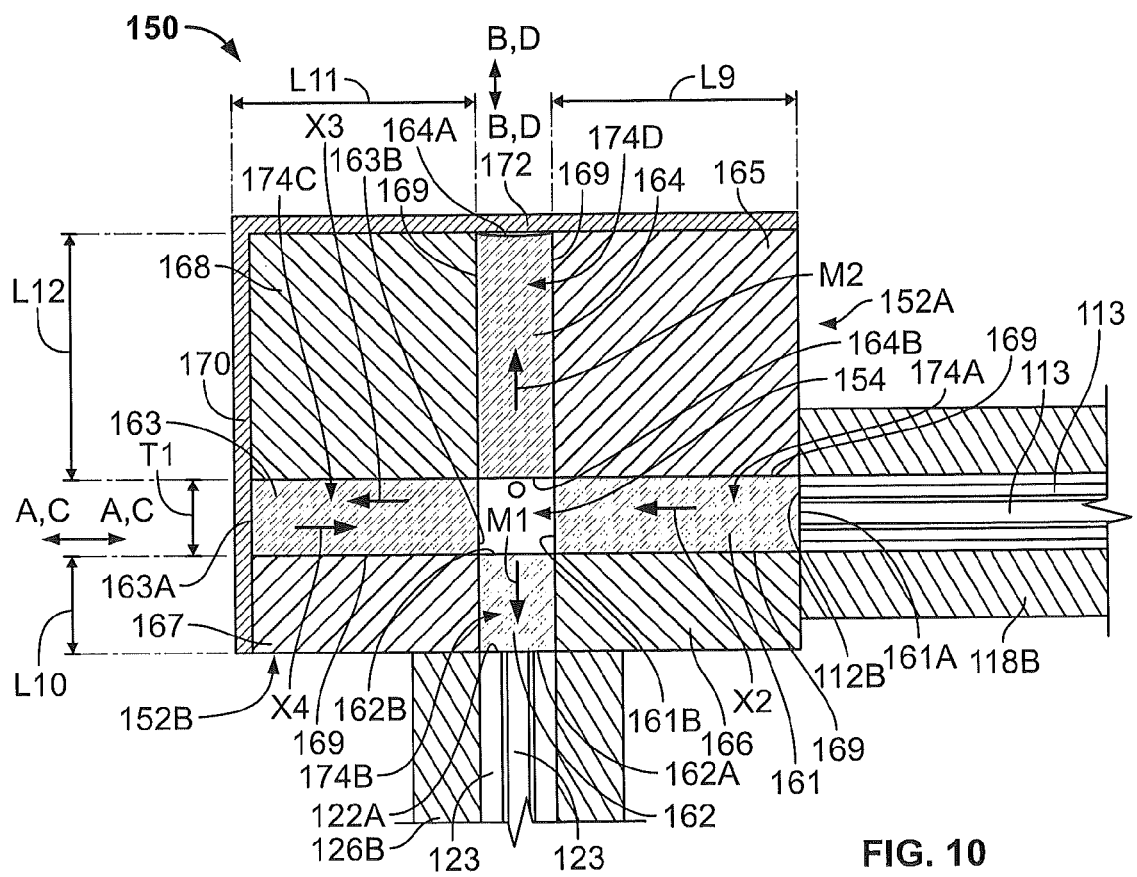
FIG. 10 is a fragmentary, cross-sectional view of the flow cell module of FIG. 4.
Figure 11:
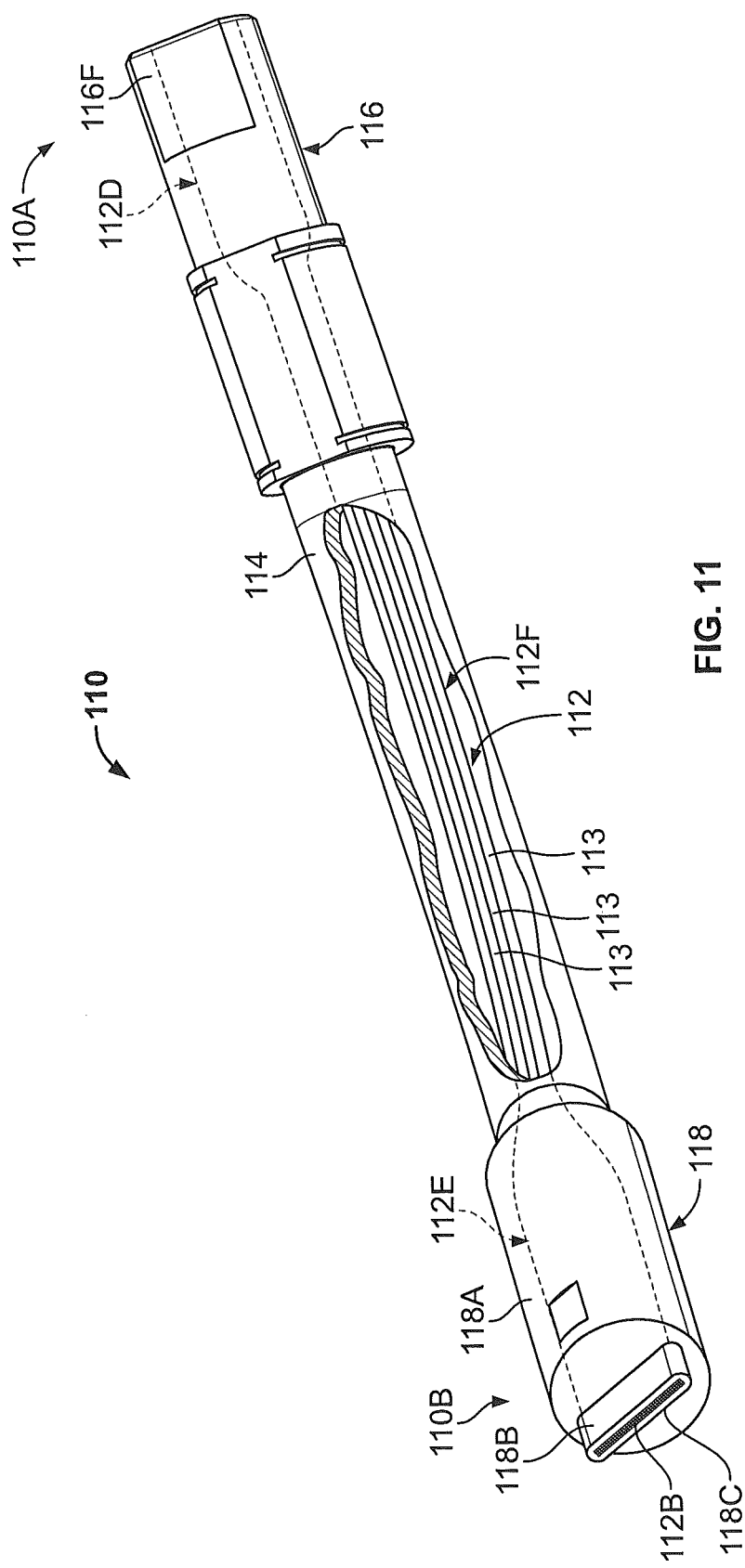
FIG. 11 is a fragmentary, perspective view of an input cable forming a part of the flow cell module of FIG. 4.
Figure 12:
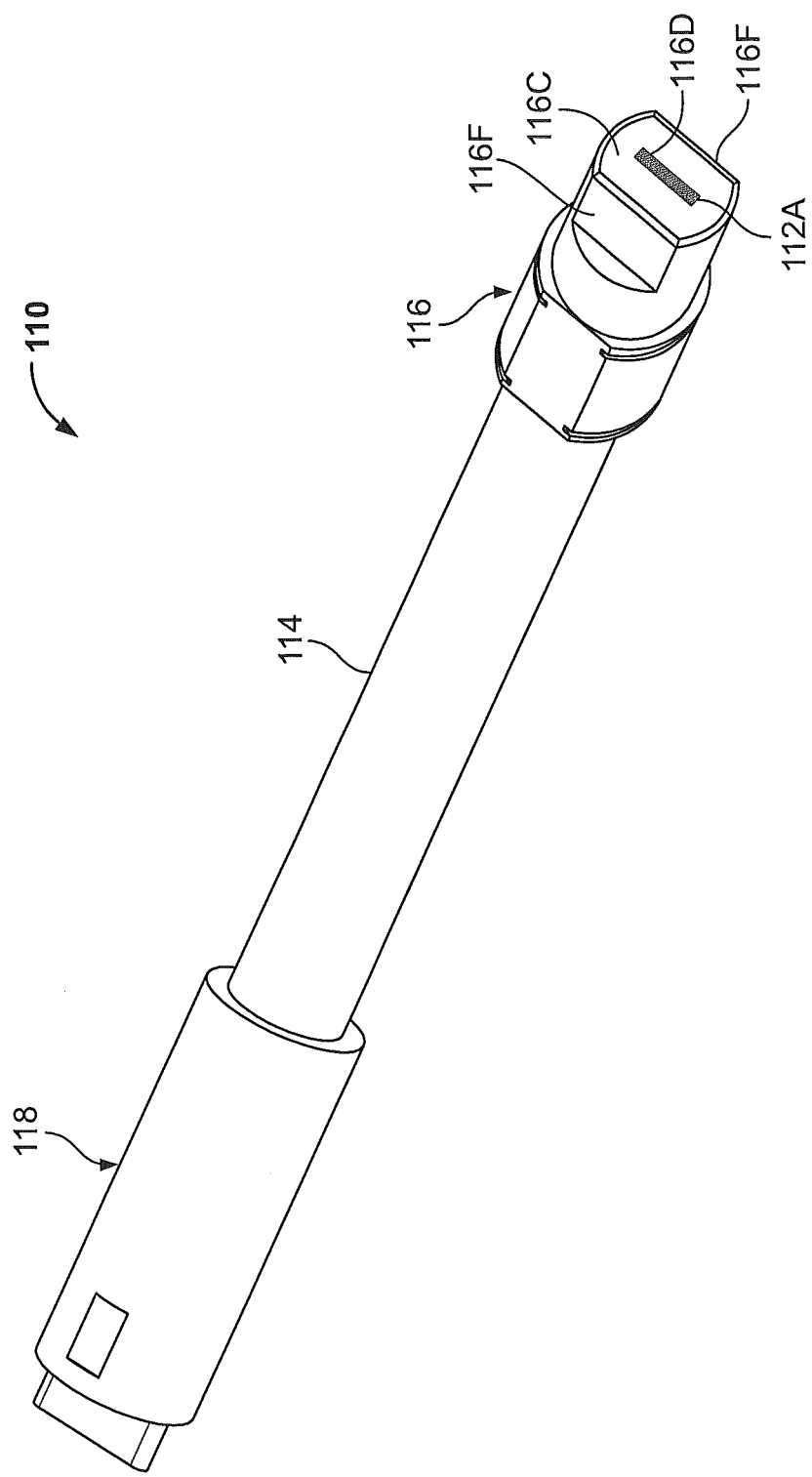
FIG. 12 is a perspective view of the input cable of FIG. 11.

With reference to FIG. 10, the waveguide block 161, and thereby the entrance light channel 174A, have a length L9. The waveguide block 162, and thereby the emission exit light channel 174B, have a length L10. The waveguide block 163, and thereby the light channel 174C, have a length L11.

The waveguide block 164, and thereby the light channel 174D, have a length L12. Each waveguide block 161-164 may have substantially the same thickness T1. The corner blocks 165-168 have thicknesses corresponding to the lengths of the waveguide blocks 161-164.

According to some embodiments, the length L10 of the emission light channel 174B is less than 1.1 mm and, in some embodiments, less than 1.0 mm. In some embodiments, the length L10 is in the range of from about 0.9 to 1.1 mm.

According to some embodiments, the length L10 of the emission light channel 174B is less than the length L9 of the entrance light channel 174A. In some embodiments, the length L10 is at least 1 mm less than the length L9 and, in some embodiments, is between about 0.5 and 2 mm less than the length L9. According to some embodiments, the length L10 of the emission light channel 174B is also less than the lengths L11 and L12 of the auxiliary light channels 174C, 174D.

Figure 7:
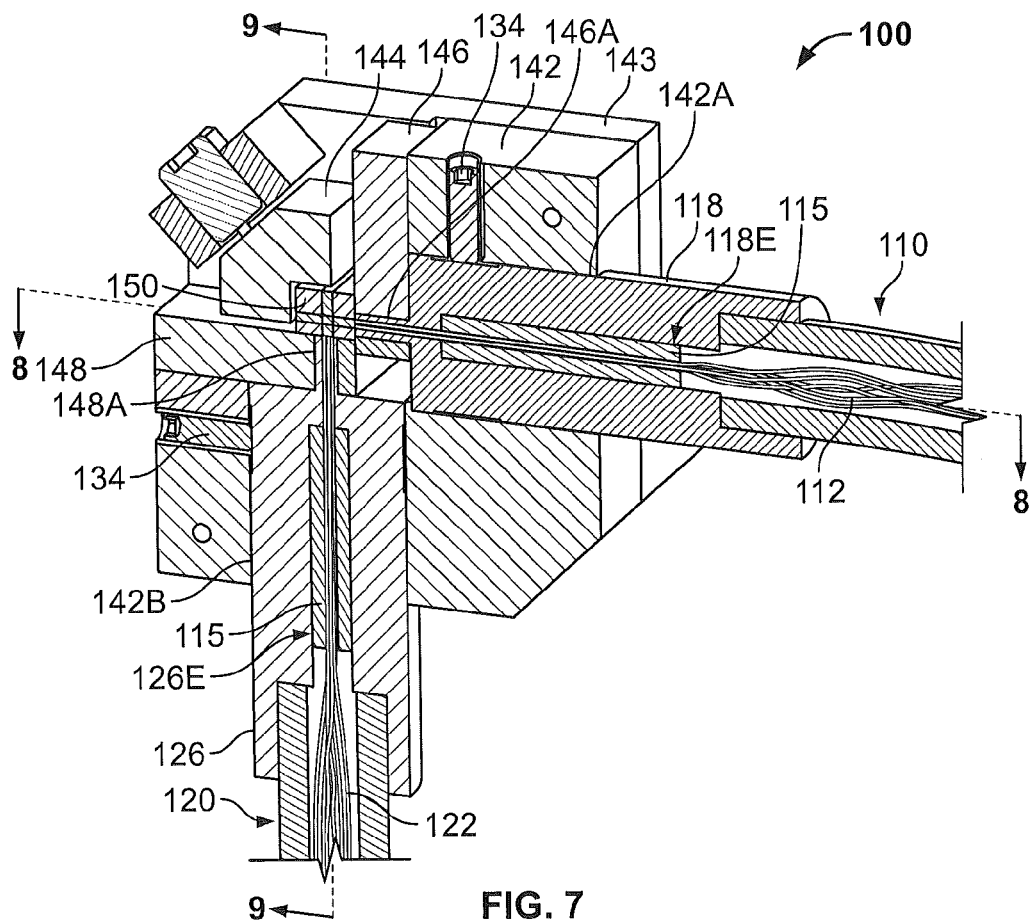
FIG. 7 is a fragmentary, cross-sectional view of the flow cell module of FIG. 4 taken along the line 7-7 of FIG. 5.
Figure 8:
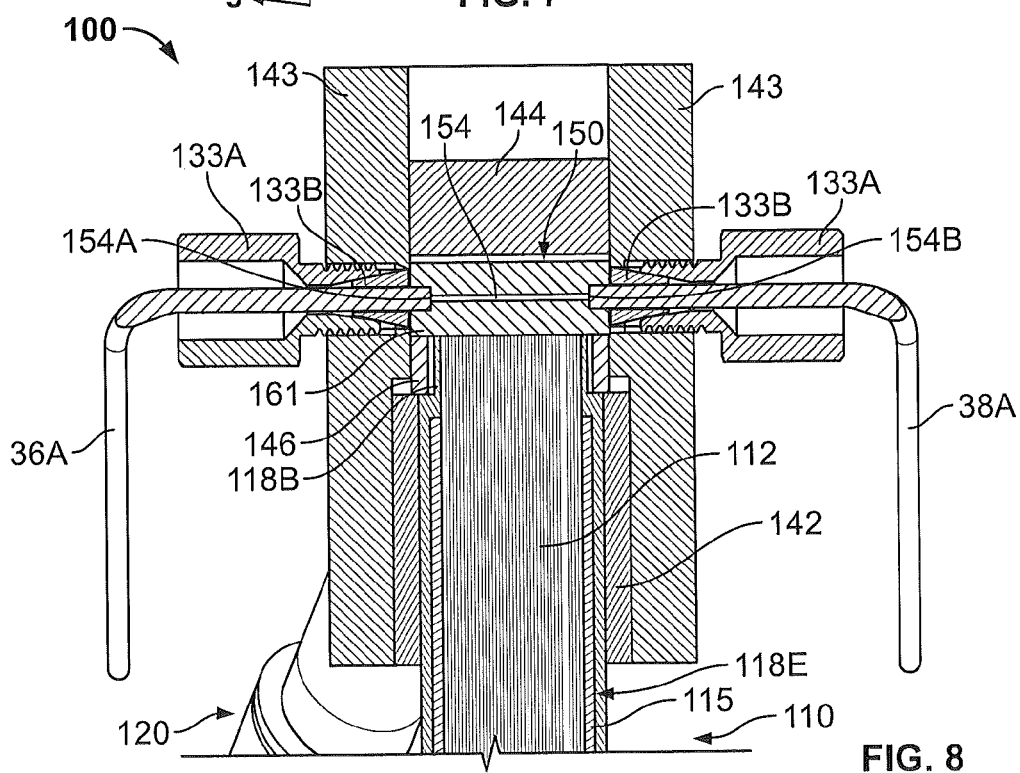
FIG. 8 is a fragmentary, cross-sectional view of the flow cell module of FIG. 4 taken along the line 8-8 of FIG. 7.
Figure 9:
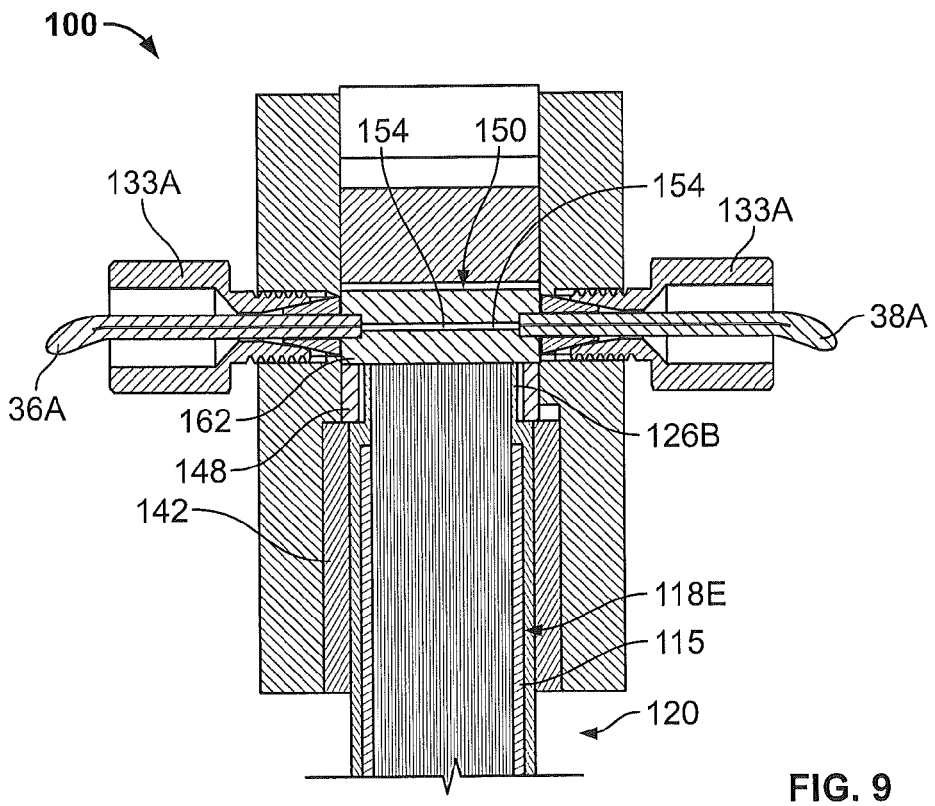
FIG. 9 is a fragmentary, cross-sectional view of the flow cell module of FIG. 4 taken along the line 9-9 of FIG. 7.

The flow cell module 100 may be assembled as follows. The side plates 143 are bolted to the frame body 142. The cable output connector 118 is inserted into the connector bore 142A and secured by a set screw 134. The cable input connector 126 is inserted into the connector bore 142B and secured by a set screw 134. The spacer 146 is installed on the cable output connector 118 and the spacer 148 is installed on the cable output connector 126 as shown in FIG. 7.

The flow cell 150 is clamped in place between the clamp block 144 and the spacers 146, 148. The output fiber bundle end face 112B is thereby aligned with and placed and retained in tight, intimate contact or abutment with the waveguide outer end face 161A. Similarly, the input fiber bundle end face 122A is thereby aligned with and placed in intimate contact or abutment with the waveguide outer end face 162A. As discussed herein, the fiber bundle end face 112B is shaped to fit or match the waveguide outer end face 161A (i.e., the excitation light entrance window) and the fiber bundle end face 122A is shaped to fit or match the waveguide outer end face 162A (i.e., the emission light exit window).

The tubes 36A and 38A may be installed in the tube bores 154C using the fittings 133A and seals 133B.

The analyzer 10 can be assembled as follows. The input connector 116 of the cable 110 is inserted into the socket 25A the output interface connector 25 of the excitation monochromator 24 and thereby mated with the output slit 24B. The set screw 25C or other securing mechanism is used secure the input connector 116. The locator features 116F of the cable connector 116 seat in the locator feature 25B of the connector 25 to prevent relative rotation. In this manner, the end face 112A is positioned and retained in alignment with and close proximity to the output slit 24B. As discussed below, the fiber bundle end face 112A is shaped to fit the output slit 24B.

The output connector 128 of the cable 120 is inserted into the input socket 35A of the connector 35 of the emission monochromator 34 and thereby mated with the input slit 34A. The retention screw 35C is used secure the output connector 128. The locator features 128F of the cable connector 128 seat in the locator feature 35B of the connector 35 to prevent relative rotation. In this manner, the end face 122B is positioned and retained in alignment with and close proximity to the input slit 34A. As discussed below, the fiber bundle end face 122B is shaped to fit the input slit 34A.

The feed tube 36A and the exit tube 38A are fluidly connected to the liquid source 36 and the liquid receiver 38, respectively.

The input port of the sensing device 30 is optically coupled to the output slit 34B of the emission monochromator 34.

The light source 20, the mirror 22 and the excitation monochromator 24 are relatively positioned such that the mirror 22 reflects (and, in some embodiments, focuses) light from the light source 20 onto the entrance slit 24A.

In use, a flow of the liquid sample is pumped or otherwise driven from the liquid sample source 36, through the feed tube 36, through the flow cell 150 (more particularly through the bore 154 from the entrance opening 154A to the exit opening 154B), through the exit tube 38, and to the liquid sample receiver 38. The liquid sample flows in contact with the waveguide block end faces 161B-164B.

Simultaneously, a beam X1 of optical energy emitted from the lamp of the source 20 is reflected off a mirror 22 and through the monochromator input slit 24A. A light beam of the selected frequency band is directed through the output slit 24B into the optical fiber cable 110 through the fiber bundle input end face 112A, and through the optical fibers 113 to the fiber bundle output end face 112B. The selected wavelength of light may be the wavelength required to excite an analyte of interest.

The light transmitted through the end face 112B enters the flow cell 150 through the surface 161A and tunnels or propagates through the waveguide block 161 as an incident excitation light beam X2 that travels toward the liquid channel 154 along the axis A-A. A portion of the light beam X2 is absorbed by the liquid in the channel (i.e., in the sample volume), including by fluorophore analytes of interest in the liquid, on the first pass of the light through the channel and will cause the fluorophores to emit light (fluoresce). However, typically another portion X3 of the light beam X2 will pass through the liquid channel 154 without being absorbed. This portion X3 then travels through the waveguide block 163 and is reflected back toward the liquid channel 154 by the mirror 170 as second pass incident light X4. A portion of the second pass incident light will likewise be absorbed by the analyte of interest, causing it to fluoresce. It will be appreciated that some of the pass-through light X3 may be absorbed by the flow cell 150 so that only a portion of the pass-through light returns to the liquid channel 154. A portion of the second pass incident light X4 is also absorbed by the liquid in the channel 154 and will cause the liquid to emit light (fluoresce).

A portion M1 of the light emitted light from the liquid sample in the liquid channel 154 will travel directly through the waveguide block 162 and the light channel 174B and into the fiber bundle input end face 122A of the cable 120. A portion M2 of the light emitted from the liquid sample in the liquid channel 154 will travel through the upper waveguide block 164 and light channel 174D and be reflected by the mirror 172 back through the waveguide block 164, the liquid channel 154, the waveguide block 162 and the emission light channel 174B and into the fiber bundle input end face 122A.

The light received through the end face 122A is transmitted through the fiber bundle 122 to the fiber bundle output end face 122B. From the end face 122B, the transmitted light enters the emission monochromator 34 through the input slit 34A. The received light (or a selected frequency band thereof) is transmitted to the sensing device 30 through the output slit 34B.

The sensing device 30 and related electronics can be used to store, monitor and analyze the received light as desired. For example, the intensity of the emitted light transmitted to through the output cable 120 may be proportional to the concentration of the measured analyte.

The analyzer 10 can be used and operated in any suitable manner. For example, the monochromators 24, 34 can be used to select or scan across excitation and emission light frequencies.

The 90 degree relative orientation between the fiber end face 112B and the fiber end face 122A can prevent or inhibit scattered excitation light from reaching the output cable 120. Likewise, the black absorbing blocks 165-168 can help to reduce or minimize scattered excitation light from reaching the output cable 120.

The mirror 170 can enhance the fluorescence signal by passing more excitation light through the sample.

The mirror 172 can enhance the fluorescence signal by enabling the flow cell 150 to collect more emission light that is initially emitted in a direction opposite the fiber end face 122A.

The waveguide block 162 constitutes the emission exit window and is relatively short or thin with a length L10 as described above. In this manner, the emission source (i.e., the fluorescing analyte) in the channel 154 is placed in close proximity to the output fiber end face 122A where the emission light is collected in order to improve or optimize emission light gathering.

The length L10 of the waveguide block 162 may be dependent on other considerations in the design of the flow cell 150. For example, the blocks 161-164 may need to be provided with a minimum length in order to prevent or inhibit scattered excitation light from entering the output fiber end face 122A. The blocks 161-164 may require a minimum thickness to withstand high pressures in the channel 154 or to withstand handling or diffusion bonding during manufacture.

The fiber bundle end faces 112A and 112B are each shaped to enhance or optimize the transmission of excitation light to the sample channel 154 from the monochromator 24, as discussed below. The fiber bundle end faces 122A and 122B are each shaped to enhance or optimize the transmission of emission light from the sample channel 154 to the monochromator 34, as discussed below.

The fiber bundle end face 112A is positioned, shaped and sized such that it fits entirely within the area of the monochromator output slit 24B. As shown, the shape and size of the optical fiber end face array 111A is smaller than that of the slit 24B. As a result, the width W3 of the end face 112A defines the monochromator's 24 true resolution. The smaller area of the end face 112A compared to that of the slit 24B helps to reduce stray light.

According to some embodiments, at least 50 percent of the area of the end face 112A overlaps the area of the slit 24B and, in some embodiments, 100 percent of the end face 112A overlaps the slit 24B.

The fiber bundle end face 112B is positioned, shaped and sized to substantially match or conform to the shape of the flow cell window face 161A. That is, the end face 112B and the window face 161A are substantially coextensive. In this manner, the cable 110 can enhance or maximize the proportion of the excitation light from the monochromator 24 that is directed into the flow cell 150 through the window 161A, and can reduce excitation light scatter.

According to some embodiments, at least 50 percent of the area of the window face 161A is covered by the end face 112B and, in some embodiments, the end face 112B overlaps 100 percent of the window face 161A. According to some embodiments, at least 50 percent of the area of the end face 112B overlaps the area of the window face 161A and, in some embodiments, 100 percent of the end face 112B overlaps the window face 161A.

In some embodiments and as shown, the dimensions of the fiber bundle end faces 112A and 112B are different from one another. In this manner, the end faces 112A, 112B can better serve their respective intended functions (as discussed above). Nonetheless, in some embodiments and as shown, the fiber bundle end faces 112A, 112B have the same total end face areas and the same number of fiber end faces 113A, 113B (i.e., all of the fibers 113 that form the end face 112A also form the end face 112B). In addition to having different dimensions, the end faces 112A, 112B may have different types of geometric shapes from one another (e.g., oval versus rectangular).

By way of example, in the illustrated cable 110, the input end face 112A has a five row array 111A (with 123 fiber end faces 113A total) and the output end face 112B has a three row array 111B (with 123 fiber end faces total). The dimensions of the input end face 112A may be 1 mm×6 mm while the dimensions of the output end face 112B are 0.5 mm×12 mm with the excitation window face 161A having dimensions of 0.5 mm×12 mm (which would provide a flow channel volume of 12 mm×0.5 mm×0.5 mm=3 microliters). Alternatively, the dimensions of the input end face 112A may be 1 mm×6 mm while the dimensions of the output end face 112B are 0.6 mm×10 mm with the excitation window face 161A having dimensions of 0.6 mm×10 mm (which would provide a flow channel volume of 10 mm×0.6 mm×0.6 mm=3.6 microliters). The dimensions of the output slit 24B may be 2 mm×8 mm and thereby oversize on all sides with respect to the 1 mm×6 mm input end face 112A.

The fiber bundle end face 122A is positioned, shaped and sized to substantially match or conform to the shape of the flow cell emission window face 162A. That is, the end face 122A and the emission window face 162A are substantially coextensive. In this manner, the cable 120 can enhance or maximize the proportion of the emission light from the flow cell 150 that is directed into the fiber bundle 122 of the cable 120 from the emission window 162A, and ultimately into the monochromator 34.

According to some embodiments, at least 50 percent of the area of the emission window face 162A is covered by the end face 122A and, in some embodiments, the end face 122A overlaps 100 percent of the emission window face 162A. According to some embodiments, at least 50 percent of the area of the end face 122A overlaps the area of the emission window face 162A and, in some embodiments, 100 percent of the end face 122A overlaps the window face 162A.

The fiber bundle end face 122B is positioned, shaped and sized such that it fits entirely within the area of the monochromator input slit 34A. As shown, the shape and size of the optical fiber end face array 121B is smaller than that of the slit 34A. The smaller area of the end face 122B compared to that of the slit 34A helps to enhance the proportion of the light transmitted by the fiber bundle 122 that is directed into the slit 34A and, in some embodiments, ensures that all of the light transmitted by the fiber bundle 122 is directed into the input slit 34A.

According to some embodiments, at least 50 percent of the area of the end face 122B overlaps the area of the slit 34A and, in some embodiments, 100 percent of the end face 122B overlaps the slit 34A.

In some embodiments and as shown, the dimensions of the fiber bundle end faces 122A and 122B are different from one another. In this manner, the end faces 122A, 122B can better serve their respective intended functions (as discussed above). Nonetheless, in some embodiments and as shown, the fiber bundle end faces 122A, 122B have the same total end face areas and the same number of fiber end faces 123A, 123B (i.e., all of the fibers 123 that form the end face 122A also form the end face 122B). In addition to having different dimensions, the end faces 122A, 122B may have different types of geometric shapes from one another (e.g., oval versus rectangular).

By way of example, in the illustrated cable 120, the input end face 122A has a three row array 121A and the output end face 122B has a five row array 121B. The dimensions of the output end face 122B may be 1 mm×6 mm while the dimensions of the input end face 122A are 0.5 mm×12 mm with the emission window face 162A having dimensions of 0.5 mm×12 mm (which would provide a flow channel volume of 12 mm×0.5 mm×0.5 mm=3 microliters). Alternatively, the dimensions of the output end face 122B may be 1 mm×6 mm while the dimensions of the input end face 122A are 0.6 mm×10 mm with the emission window face 162A having dimensions of 0.6 mm×10 mm (which would provide a flow channel volume of 10 mm×0.6 mm×0.6 mm=3.6 microliters). The dimensions of the input slit 34A may be 2 mm×8 mm and thereby oversize on all sides with respect to the 1 mm×6 mm output end face 122B.

The dimensions and shapes of the fiber bundle end faces 112A, 112B, 122A, 122B can be selected to match the light ports 24B, 34A of monochromators 24, 34 (or other optical devices) and flow cell windows 161A, 162A of different sizes and shapes. This may be accomplished by selection of the number of optical fibers 113, 123 in the cable bundle 112, 122, the sizes of the optical fibers 113, 123, and or the layout of the optical fibers 113, 123.

According to some embodiments, the length of each cable 110, 120 is in the range of from about 5 to 50 cm. Notably, the flexibility of the connectorized fiber optic cables 110, 120 can permit a relatively compact configuration.

According to some embodiments, the liquid sample is flowed through the liquid channel 154 at a rate in the range of from about 0.5 to 1.5 ml/min.

According to some embodiments, the liquid channel 154 has a volume of less than 2 microliters and, in some embodiments, in the range of from about 2 to 5 microliters.

According to some embodiments, the flow cell 150 can withstand a working pressure in the liquid channel 154 (without leak or failure of the flow cell 150) of at least 500 psi and, in some embodiments, at least 2000 psi.

Suitable excitation and emission monochromators 24, 34 for the analyzer 10 may include Horiba JY 1034B monochromators. In some embodiments, the monochromators 24, 34 have an F-number of 2.0 and a numerical aperture of at least 0.24. The monochromators 24, 34 may have an integral motor drive (e.g., a stepper motor) to implement wavelength scanning.

Figure 23:
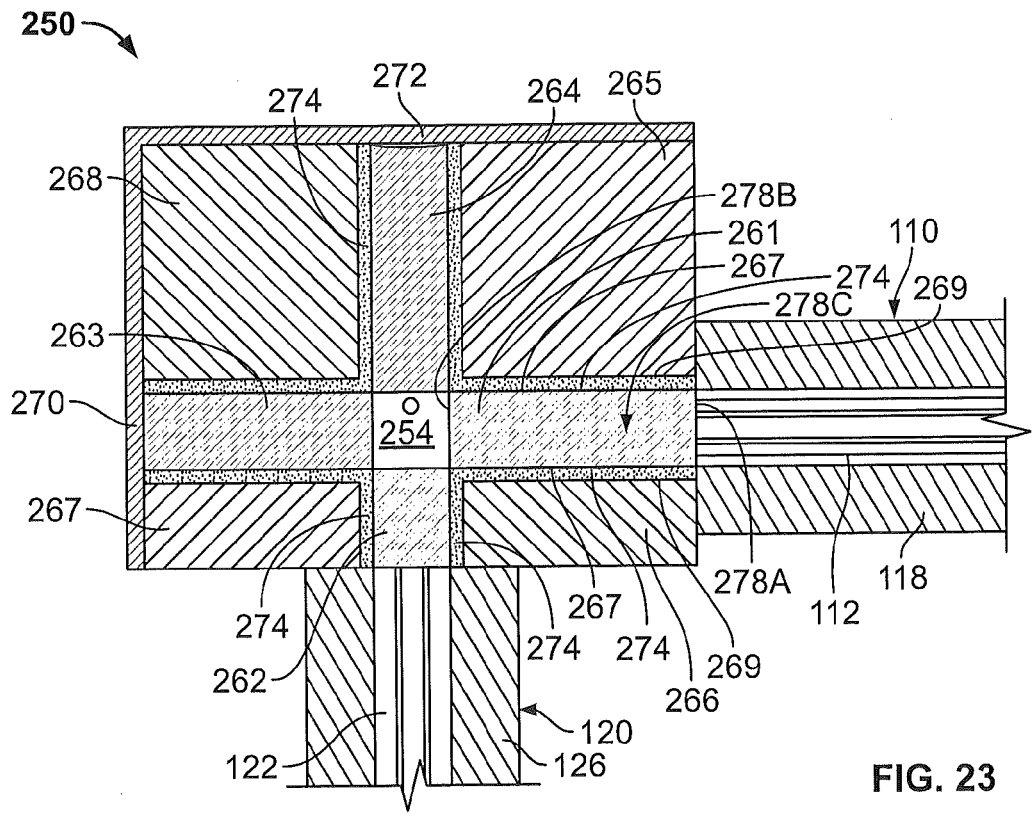
FIG. 23 is a fragmentary, cross-sectional view of a flow cell module according to further embodiments of the technology.

With reference to FIG. 23, an alternative flow cell 250 according to further embodiments of the invention is shown therein. The flow cell 250 may be used in place of the flow cell 150. However, for the purpose of explanation only the interfacing ends of the fiber optic cables 110, 120 are shown in FIG. 23.

The flow cell 250 includes waveguide blocks 261-264, corner blocks 265-268, and mirror layers 270, 272 corresponding to waveguide blocks 161-164, corner blocks 165-168, and mirror layers 170, 172, respectively. The flow cell 250 defines a liquid flow channel 254 corresponding to the flow channel 154.

The flow cell 250 differs from the flow cell 150 in that layers of adhesive 274 are interposed between and bond the opposed surfaces 269 and 267 of the adjacent waveguide blocks 261-264 and the corner blocks 265-268 to one another. Each waveguide block 261-264 and the adhesive layers 274 bonded thereto constitute a waveguide. The adhesive 274 has a lower refractive index than the refractive index of the material (e.g., fused silica) of the waveguide blocks 261-264. As a result, the waveguide blocks 261-264 serve as optical cores and the adhesive layers 274 serve as optical cladding. According to some embodiments, the adhesive cladding layers 274 provide total internal reflection (TIR) to the light channels. The adhesive cladding layers 274 are planar and continuous. The inner surface of each adhesive layer 274 is in intimate contact or abutment with the outer surface 269 of the waveguide block 261-264 it surrounds. The inner surface of the cladding layer 274 defines a passage or bore 278C extending axially to the flow channel 254 and terminating at opposed end openings 278A, 278B. The TIR of the light channels reduces loss of excitation and emission light to undesirable absorption in the flow cell 250.

Any suitable type of adhesive may be used for the adhesive layers 274. In some embodiments, the adhesive 274 is a silicone adhesive and, in some embodiments, a thermally cured silicone adhesive. Suitable adhesives may include SCHOTT Deep UV-200 silicone adhesive available from SCHOTT North America, Inc. of Pennsylvania.

Figure 24:
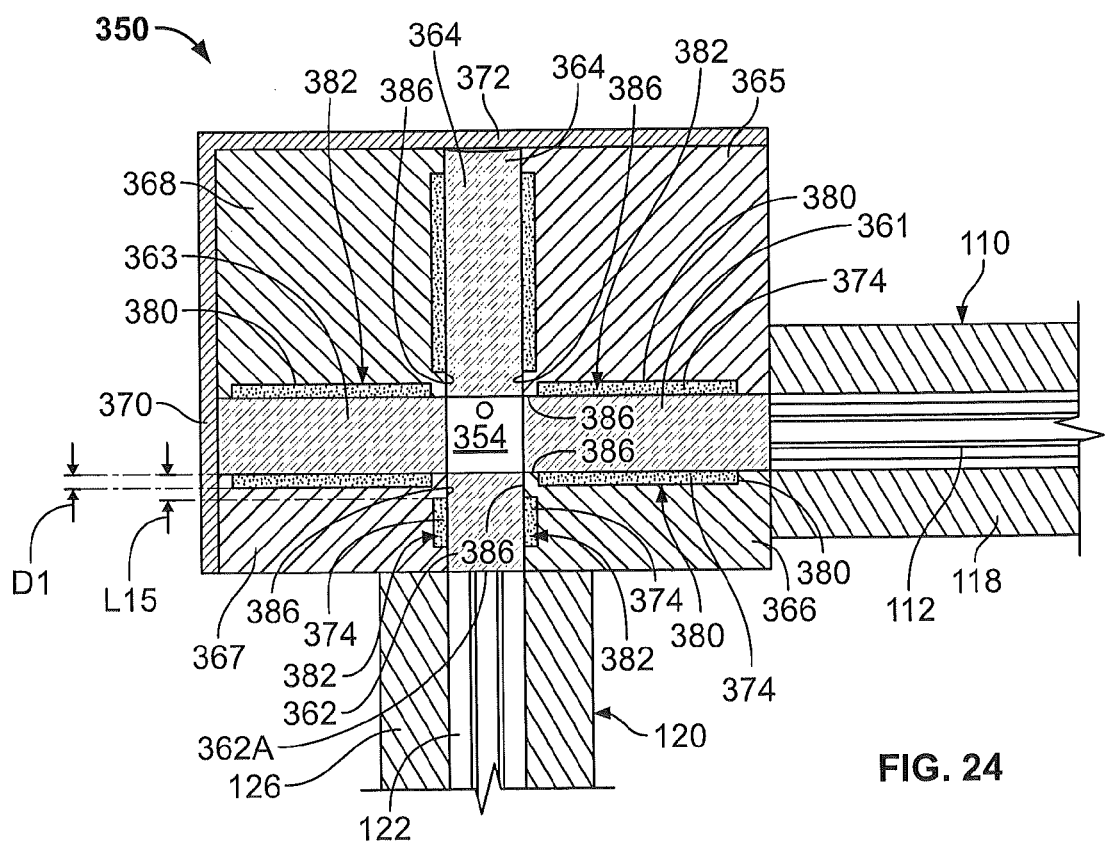
FIG. 24 is a fragmentary, cross-sectional view of a flow cell module according to further embodiments of the technology.
Figure 25:
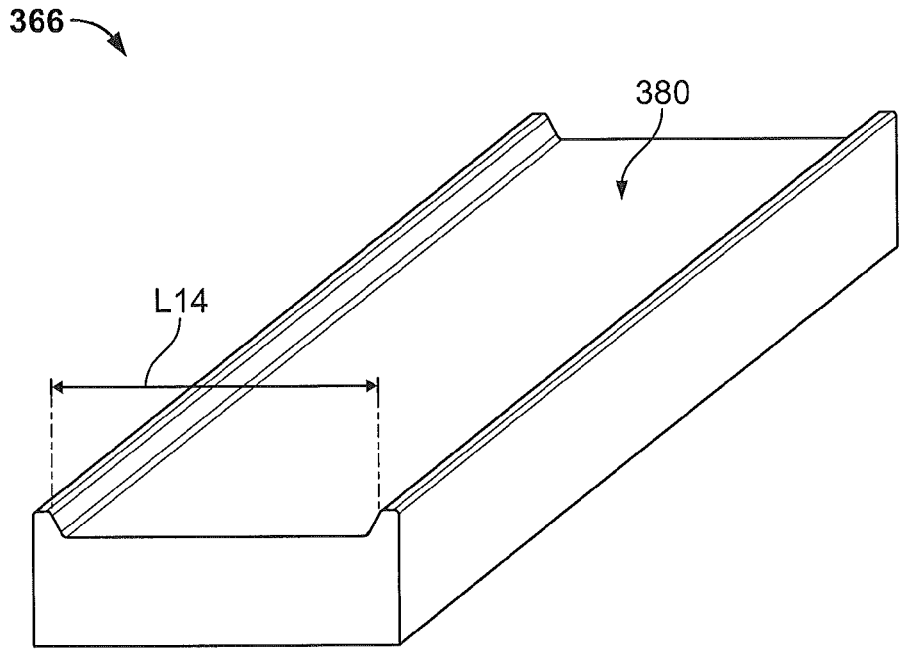
FIG. 25 is a perspective view of a corner block forming a part of the flow cell module of FIG. 24.

With reference to FIGS. 24 and 25, an alternative flow cell 350 according to further embodiments of the invention is shown therein. The flow cell 350 may be used in place of the flow cell 150. However, for the purpose of explanation only the interfacing ends of the fiber optic cables 110, 120 are shown in FIG. 24.

The flow cell 350 includes waveguide blocks 361-364, corner blocks 365-368, and mirror layers 370, 372, and adhesive layers 374 corresponding to waveguide blocks 261-264, corner blocks 265-268, mirror layers 270, 272, and adhesive layers 274, respectively. The flow cell 350 defines a liquid flow channel 354 corresponding to the flow channel 254.

The flow cell 350 differs from the flow cell 250 in that each of the corner blocks 365-368 includes shallow grooves, cavities or pockets 380 formed in each of its engagement faces 367. The waveguide blocks 361-364 close the pockets 380 to define enclose chambers 382 in which the adhesive layers 374 are contained. The waveguide blocks 361-364 and the adhesive layers 374 cooperatively constitute waveguides and, in some embodiments, cooperate to provide TIR as discussed above.

End pads 386 of the corner blocks 365-368 directly engage end portions of the waveguide blocks 361-364. The end pads 386 are formed of an opaque, light absorbing material and can thereby serve to prevent or inhibit excitation light from the excitation cable 110 from propagating directly through the emission window 362A to the emission cable 120.

Each pocket 380 will typically extend along the full length of the flow channel 354. According to some embodiments, each pocket 380 has a depth D1 in the range of from about 0.01 to 0.03 mm. According to some embodiments, each pocket 380 has a length L14 in the range of from about 1 to 2 mm.

Each end pad 386 will typically extend along the full length of the flow channel 354. According to some embodiments, each end pad 386 has a length L15 in the range of from about 0.3 to 0.5 mm. The end pads 386 may be integral and, in some embodiments, monolithic with the corner blocks 365-368.

Figure 26:
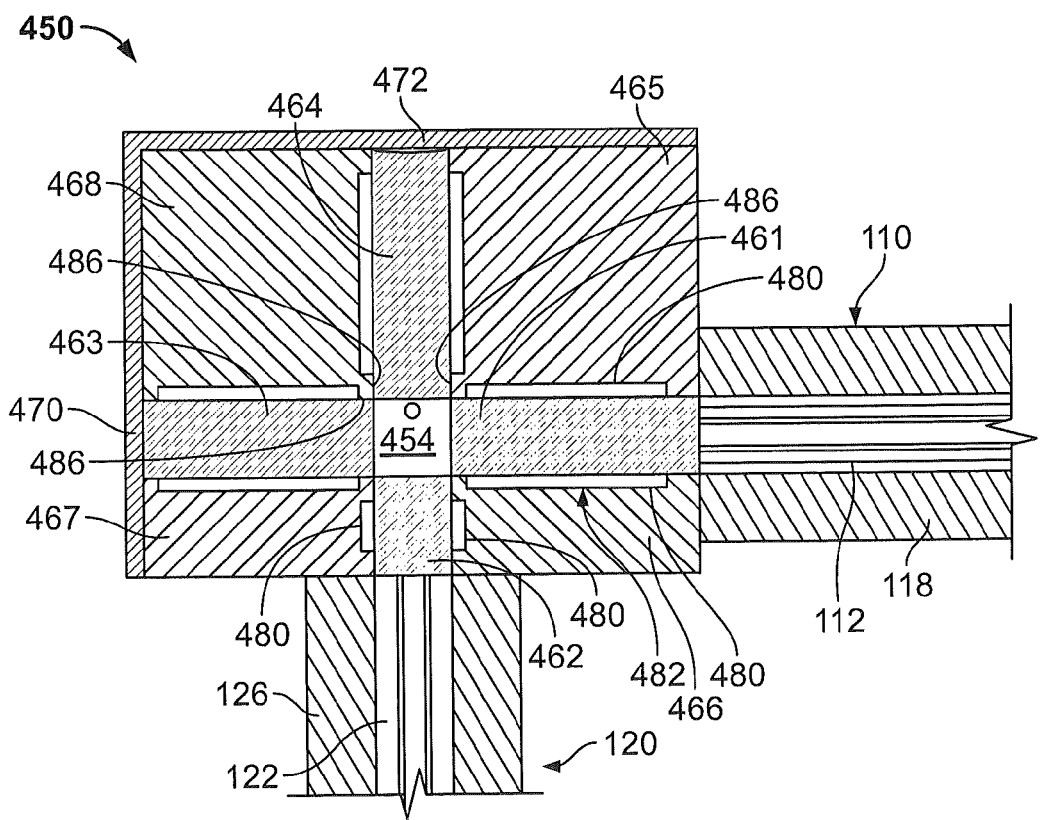
FIG. 26 is a fragmentary, cross-sectional view of a flow cell module according to further embodiments of the technology.

With reference to FIG. 26, an alternative flow cell 450 according to further embodiments of the invention is shown therein. The flow cell 450 may be used in place of the flow cell 150. However, for the purpose of explanation only the interfacing ends of the fiber optic cables 110, 120 are shown in FIG. 26.

The flow cell 450 includes waveguide blocks 461-464, corner blocks 465-468, and mirror layers 470, 472 corresponding to waveguide blocks 361-364, corner blocks 365-368 and mirror layers 370, 372, respectively. The flow cell 450 defines a liquid flow channel 454 corresponding to the flow channel 354.

The flow cell 450 differs from the flow cell 350 in that the pockets 480 of the flow cell 450 are not filled with adhesive. Rather, the chambers 482 defined by the pockets 480 and the waveguide blocks 461-464 are filled with air having a lower refractive index than the material of the waveguide blocks 461-464. Alternatively, the chambers 482 may be filled with a gas other than air having a lower refractive index than the material of the waveguide blocks 461-464. The end pads 486 may be bonded (e.g., contact bonded) to the waveguide blocks 461-464 to secure the waveguide blocks 461-464 to the corner blocks 465-468.

Figure 27:
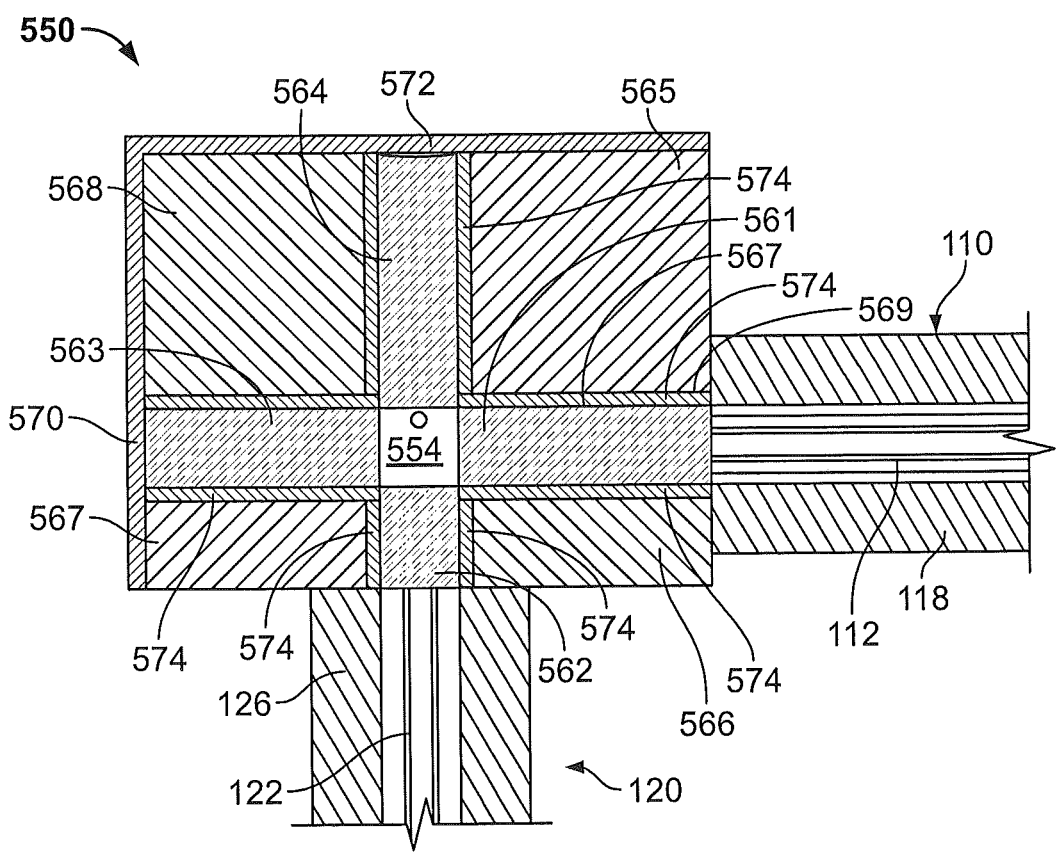
FIG. 27 is a fragmentary, cross-sectional view of a flow cell module according to further embodiments of the technology.

With reference to FIG. 27, an alternative flow cell 550 according to further embodiments of the invention is shown therein. The flow cell 550 may be used in place of the flow cell 150. However, for the purpose of explanation only the interfacing ends of the fiber optic cables 110, 120 are shown in FIG. 27.

The flow cell 550 includes waveguide blocks 561-564, corner blocks 565-568, and mirror layers 570, 572 corresponding to waveguide blocks 261-264, corner blocks 265-268, and mirror layers 270, 272, respectively. The flow cell 550 defines a liquid flow channel 554 corresponding to the flow channel 254.

The flow cell 550 differs from the flow cell 250 in that cladding layers 574 are interposed between the opposed surfaces 569 and 567 of the adjacent waveguide blocks 561-564 and the corner blocks 565-568. The cladding layers 574 are formed of a fluoropolymer and, in some embodiments, an amorphous fluoropolymer. According to some embodiments, the cladding layers 574 are formed of an amorphous copolymer of perfluora-2,2-dimethyl-1,3-dioxole and tetrafluoroethylene, an example of which is sold by E.I. du Pont de Nemours (commonly referred to as DuPont) under the trademark Teflon AF 2400™. The cladding layers have a lower refractive index than the refractive index of the material (e.g., fused silica) of the waveguide blocks 561-564. As a result, the waveguide blocks serve as cores and the adhesive layers 574 serve as optical cladding providing, in some embodiments, total internal reflection to the light channels.

Flow cells of the present technology, particularly when formed as discussed hereinabove to provide total internal reflection, allow for a smaller volume flow cell without loss of optical signal, thereby increasing output resolution.

In particular, the TIR can reduce light losses and maximize light flux to and from the flow cell windows. In some embodiments, the provision of TIR may reduce or eliminate the need for a reduced length emission waveguide channel as described above. The TIR waveguides can provide greater flexibility in the design of the flow cell.

Liquid sample analyzers and flow cell assemblies according to embodiments of the technology can provide a number of benefits and advantages. Sensing devices such as PDA spectrometers typically require low flow cell dispersion and fast data rates and high light flux. It is desirable to provide a flow cell assembly that is compact and that can be flexibly integrated into a PDA spectrometer system.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims, therefore, are to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

What is claimed:

1. A flow cell for a fluorescence spectrometer, the flow cell comprising:
   a flow channel to receive a flow of a liquid sample;
   an excitation light entrance window to receive excitation light from a light source; and
   an emission light exit window to transmit fluorescent emission light from the liquid sample in the flow channel from the flow cell;
   wherein the excitation light entrance window and/or emission light exit window includes a waveguide including:
      a waveguide core formed of a core material and having an inner end face; and
      a cladding medium surrounding a portion of the waveguide core, wherein the cladding medium has a refractive index less than the refractive index of the core material;
   wherein the inner end face of the waveguide:
      defines a portion of the flow channel;
      serves as a light input port for the excitation light into the flow channel or a light output port for the fluorescent emission light out of the flow channel; and
      contacts the liquid sample in the flow channel; and
   wherein the flow cell includes an end pad of opaque, light absorbing material surrounding an end portion of the waveguide core adjacent the flow channel and adjacent the inner end face of the waveguide, wherein the end pad prevents light from propagating directly from the excitation light entrance window to the excitation light exit window.

2. The flow cell of claim 1 wherein the core material is fused silica or quartz.

3. The flow cell of claim 1 wherein the waveguide has total internal reflection.

4. The flow cell of claim 1 wherein the cladding medium is a fluoropolymer.

5. The flow cell of claim 1 wherein the cladding medium is an adhesive.

6. The flow cell of claim 1 wherein the cladding medium is air.

7. The flow cell of claim 1 wherein:
   the flow cell includes a flow cell body; and
   the cladding medium is interposed between the flow cell body and the waveguide core.

8. The flow cell of claim 7 wherein:
   the flow cell body includes an integral pocket; and
   the waveguide core and the pocket collectively form a chamber containing the cladding medium.

9. The flow cell of claim 7 wherein the flow cell body is formed of fused silica or quartz.

10. The flow cell of claim 7 wherein the waveguide is directly bonded to the flow cell body.

11. The flow cell of claim 10 wherein the cladding medium is an adhesive, and the adhesive bonds the waveguide core to the flow cell body.

12. The flow cell of claim 10 wherein the waveguide is contact bonded to the flow cell body such that interfacing surfaces of the waveguide and the flow cell body diffuse into one another.

13. The flow cell of claim 1 wherein the emission light exit window is oriented at an angle of about 90 degrees with respect to the excitation light entrance window.

14. The flow cell of claim 1 wherein the waveguide extends from the flow cell to an optical device.

15. The flow cell of claim 14 wherein the optical device is at least one of a light source, a monochromator, and a fluorescence detector.

16. The flow cell of claim 14 wherein the waveguide is a flexible optical fiber.

17. The flow cell of claim 14 wherein the excitation light entrance window and/or emission light exit window includes an optical fiber bundle including a plurality of flexible optical fibers.

18. The flow cell of claim 1 wherein:
the waveguide is an excitation light entrance window waveguide;
the inner end face of the excitation light entrance window waveguide serves as a light input port for the excitation light into the flow channel;
the emission light exit window includes an emission light exit window waveguide including:
a waveguide core formed of a core material and having an inner end face; and
a cladding medium surrounding a portion of the waveguide core, wherein the cladding medium has a refractive index less than the refractive index of the core material; and
the inner end face of the emission light exit window waveguide:
defines a portion of the flow channel;
serves as a light output port for the fluorescent emission light out of the flow channel; and
contacts the liquid sample in the flow channel.

19. The flow cell of claim 18 wherein the inner end face of the excitation light entrance window waveguide is oriented at an angle of about 90 degrees with respect to the inner end face of the emission light exit window waveguide.

20. The flow cell of claim 19 wherein the inner end face of the excitation light entrance window waveguide and the inner end face of the emission light exit window waveguide abut one another at the flow channel to form an axially extending corner of the flow channel.

21. The flow cell of claim 18 wherein:
the emission light exit window waveguide includes an outer end face opposite its inner end face; and
the outer end face of the emission light exit window is located less than 1.0 mm from the flow channel.

22. The flow cell of claim 1 wherein:
the excitation light entrance window waveguide includes an outer end face opposite its inner end face;
the emission light exit window waveguide includes an outer end face opposite its inner end face;
the outer end face of the excitation light entrance window waveguide is spaced a first distance from the flow channel;
the outer end face of the emission light exit window waveguide is spaced a second distance from the flow channel; and
the second distance is less than the first distance.

23. The flow cell of claim 1 including:
a second waveguide disposed opposite the first waveguide across the flow channel;
wherein the second waveguide includes:
a waveguide core formed of a core material and having an inner end face; and
a cladding medium surrounding a portion of the waveguide core, wherein the cladding medium has a refractive index less than the refractive index of the core material; and
wherein the inner end face of the second waveguide:
defines a portion of the flow channel; and
contacts the liquid sample in the flow channel.

24. The flow cell of claim 23 including a mirror positioned to reflect light that has passed through the second waveguide from the liquid sample back into the liquid sample.

25. A method for analyzing a liquid sample using a fluorescence spectrometer, the method comprising:
providing a flow cell including:
a flow channel to receive a flow of a liquid sample;
an excitation light entrance window to receive excitation light from a light source; and
an emission light exit window to transmit fluorescent emission light from the liquid sample in the flow channel from the flow cell;
wherein the excitation light entrance window and/or emission light exit window includes a waveguide including:
a waveguide core formed of a core material and having an inner end face; and
a cladding medium surrounding a portion of the waveguide core, wherein the cladding medium has a refractive index less than the refractive index of the core material; and
wherein the inner end face of the waveguide:
defines a portion of the flow channel;
serves as a light input port for the excitation light into the flow channel or a light output port for the fluorescent emission light out of the flow channel; and
contacts the liquid sample in the flow channel; and
wherein the flow cell includes an end pad of opaque, light absorbing material surrounding an end portion of the waveguide core adjacent the flow channel and adjacent the inner end face of the waveguide, wherein the end pad prevents light from propagating directly from the excitation light entrance window to the excitation light exit window;
introducing the liquid sample into the flow channel such that the liquid sample contacts the inner end face of the waveguide; and
directing excitation light from the light source into the liquid sample in the flow channel through the excitation light entrance window.

26. A flow cell for a fluorescence spectrometer, the flow cell comprising:
a flow channel to receive a flow of a liquid sample;
an excitation light entrance window to receive excitation light from a light source; and
an emission light exit window to transmit fluorescent emission light from the liquid sample in the flow channel from the flow cell;

wherein the excitation light entrance window and/or emission light exit window includes a waveguide including:
  a waveguide core formed of a core material and having an inner end face; and
  a cladding medium surrounding a portion of the waveguide core, wherein the cladding medium has a refractive index less than the refractive index of the core material;
wherein the inner end face of the waveguide:
  defines a portion of the flow channel;
  serves as a light input port for the excitation light into the flow channel or a light output port for the fluorescent emission light out of the flow channel; and
  contacts the liquid sample in the flow channel;
wherein the waveguide is directly bonded to the flow cell body; and
wherein the waveguide is contact bonded to the flow cell body such that interfacing surfaces of the waveguide and the flow cell body diffuse into one another.

27. A flow cell for a fluorescence spectrometer, the flow cell comprising:
a flow channel to receive a flow of a liquid sample;
an excitation light entrance window to receive excitation light from a light source; and
an emission light exit window to transmit fluorescent emission light from the liquid sample in the flow channel from the flow cell;
wherein the excitation light entrance window and/or emission light exit window includes:
  a first waveguide including:
    a first waveguide core formed of a first core material and having a first inner end face; and
    a first cladding medium surrounding a portion of the first waveguide core, wherein the first cladding medium has a refractive index less than the refractive index of the first core material; and
  a second waveguide disposed opposite the first waveguide across the flow channel, the second waveguide including:
    a second waveguide core formed of a second core material and having a second inner end face; and
    a second cladding medium surrounding a portion of the second waveguide core, wherein the second cladding medium has a refractive index less than the refractive index of the second core material; and
wherein the first inner end face of the first waveguide:
  defines a portion of the flow channel;
  serves as a light input port for the excitation light into the flow channel or a light output port for the fluorescent emission light out of the flow channel; and
  contacts the liquid sample in the flow channel; and
wherein the second inner end face of the second waveguide:
  defines a portion of the flow channel; and
  contacts the liquid sample in the flow channel; and
wherein the flow cell includes a mirror positioned to reflect light that has passed through the second waveguide from the liquid sample back into the liquid sample.

* * * * *